(12) United States Patent (10) Patent No.: US 8,481,546 B2
Chaturvedula et al. (45) Date of Patent: Jul. 9, 2013

(54) CGRP RECEPTOR ANTAGONIST

(75) Inventors: Prasad V. Chaturvedula, Cheshire, CT (US); Gene M. Dubowchik, Middlefield, CT (US); John E. Macor, Guilford, CT (US)

(73) Assignee: Bristol-Myers Squibb Company, Princeton, NJ (US)

( * ) Notice: Subject to any disclaimer, the term of this patent is extended or adjusted under 35 U.S.C. 154(b) by 219 days.

(21) Appl. No.: 13/038,550

(22) Filed: Mar. 2, 2011

(65) Prior Publication Data

US 2012/0059017 A1 Mar. 8, 2012

Related U.S. Application Data

(60) Provisional application No. 61/319,015, filed on Mar. 30, 2010.

(51) Int. Cl.
*C07D 401/14* (2006.01)
*A61K 31/496* (2006.01)

(52) U.S. Cl.
USPC .................................... 514/253.07; 544/363

(58) Field of Classification Search
None
See application file for complete search history.

(56) References Cited

U.S. PATENT DOCUMENTS 7,220,862 B2 5/2007 Chaturvedula et al.

FOREIGN PATENT DOCUMENTS

WO WO 03/104236 12/2003

OTHER PUBLICATIONS

Benarroch, Neurology, vol. 77, No. 3, pp. 281-287 (2011) (Abstract provided).*

Paone, D.V. et al., "Calcitonin gene-related peptide receptor antagonists for the treatment of migraine: a patent review", Expert Opin. Ther. Patents, vol. 19, No. 12, pp. 1675-1713 (2009).

* cited by examiner

*Primary Examiner* — Emily Bernhardt
(74) *Attorney, Agent, or Firm* — James Epperson

(57) ABSTRACT

The disclosure generally relates to the compound of formula I, (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, including pharmaceutically acceptable salts, which is a CGRP-receptor antagonist. The disclosure also relates to pharmaceutical compositions and methods for using the compound in the treatment of CGRP related disorders including migraine headaches, neurogenic vasodilation, neurogenic inflammation, thermal injury, circulatory shock, flushing associated with menopause, airway inflammatory diseases such as asthma, chronic obstructive pulmonary disease (COPD), and cancer.

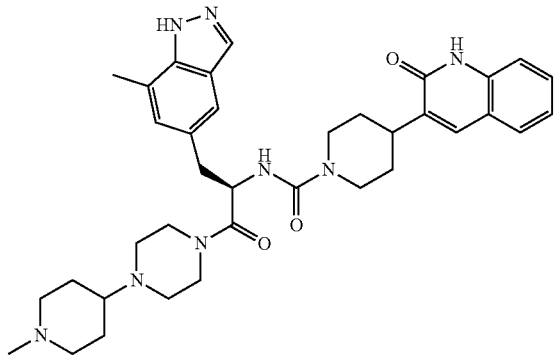

3 Claims, No Drawings

CGRP RECEPTOR ANTAGONIST

CROSS REFERENCE TO RELATED APPLICATIONS

This patent application claims the benefit of U.S. provisional patent application No. 61/319,015 filed Mar. 30, 2010.

BACKGROUND OF THE INVENTION

The disclosure generally relates to the compound (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (Compound I or the compound of formula I), including pharmaceutically acceptable salts, which is a CGRP-receptor antagonist. The disclosure also relates to pharmaceutical compositions and methods for using the compound in the treatment of CGRP related disorders including migraine headaches, neurogenic vasodilation, neurogenic inflammation, thermal injury, circulatory shock, flushing associated with menopause, airway inflammatory diseases such as asthma, chronic obstructive pulmonary disease (COPD), and cancer.

Calcitonin gene-related peptide (CGRP) is a naturally occurring 37-amino-acid peptide first identified in 1982 (Amara, S. G. et al, Science 1982, 298, 240-244). Two forms of the peptide are expressed (aCGRP and (CGRP) which differ by one and three amino acids in rats and humans, respectively. The peptide is widely distributed in both the peripheral (PNS) and central nervous system (CNS), principally localized in sensory afferent and central neurons, and displays a number of biological effects, including vasodilation.

When released from the cell, CGRP binds to specific cell surface G protein-coupled receptors and exerts its biological action predominantly by activation of intracellular adenylate cyclase (Poyner, D. R. et al, Br J Pharmacol 1992, 105, 441-7; Van Valen, F. et al, Neurosci Lett 1990, 119, 195-8.). Two classes of CGRP receptors, CGRP1 and CGRP2, have been proposed based on the antagonist properties of the peptide fragment CGRP (8-37) and the ability of linear analogues of CGRP to activate CGRP2 receptors (Juaneda, C. et al. TiPS 2000, 21, 432-438). However, there is lack of molecular evidence for the CGRP2 receptor (Brain, S. D. et al, TiPS 2002, 23, 51-53). The CGRP1 receptor has three components: (i) a 7 transmembrane calcitonin receptor-like receptor (CRLR); (ii) the single transmembrane receptor activity modifying protein type one (RAMP1); and (iii) the intracellular receptor component protein (RCP) (Evans B. N. et al., J Biol Chem. 2000, 275, 31438-43). RAMP 1 is required for transport of CRLR to the plasma membrane and for ligand binding to the CGRP-receptor (McLatchie, L. M. et al, Nature 1998, 393, 333-339). RCP is required for signal transduction (Evans B. N. et al., J Biol Chem. 2000, 275, 31438-43). There are known species-specific differences in binding of small molecule antagonists to the CGRP-receptor with typically greater affinity seen for antagonism of the human receptor than for other species (Brain, S. D. et al, TiPS 2002, 23, 51-53). The amino acid sequence of RAMP1 determines the species selectivity, in particular, the amino acid residue Trp74 is responsible for the phenotype of the human receptor (Mallee et al. J Biol Chem 2002, 277, 14294-8).

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001; 15(10): 745-53; Williamson, D. J. Microsc. Res. Tech. 2001, 53, 167-178.; Grant, A. D. Brit. J. Pharmacol. 2002, 135, 356-362.). Serum levels of CGRP are elevated during migraine (Goadsby P J, et al. Ann Neurol 1990; 28:183-7) and treatment with anti-migraine drugs returns CGRP levels to normal coincident with alleviation of headache (Gallai V. et al. Cephalalgia 1995; 15: 384-90). Migraineurs exhibit elevated basal CGRP levels compared to controls (Ashina M, et al., Pain 2000, 86(1-2):133-8.2000). Intravenous CGRP infusion produces lasting headache in migraineurs (Lassen L H, et al. Cephalalgia 2002 February; 22(1):54-61). Preclinical studies in dog and rat report that systemic CGRP blockade with the peptide antagonist CGRP (8-37) does not alter resting systemic hemodynamics nor regional blood flow (Shen, Y-T. et al, J Pharmacol Exp Ther 2001, 298, 551-8). Thus, CGRP-receptor antagonists may present a novel treatment for migraine that avoids the cardiovascular liabilities of active vasoconstriction associated with non-selective 5-HT1B/1D agonists, 'triptans' (e.g., sumatriptan).

CGRP antagonists have shown efficacy in human clinical trials. See Davis C D, Xu C. *Curr Top Med Chem.* 2008 8(16):1468-79; Benemei S, Nicoletti P, Capone J G, Geppetti P. *Curr Opin Pharmacol.* 2009 9(1):9-14. Epub 2009 Jan. 20; Ho T W, Ferrari M D, Dodick D W, Galet V, Kost J, Fan X, Leibensperger H, Froman S, Assaid C, Lines C, Koppen H, Winner P K. *Lancet.* 2008 372:2115. Epub 2008 Nov. 25; Ho T W, Mannix L K, Fan X, Assaid C, Furtek C, Jones C J, Lines C R, Rapoport A M; *Neurology* 2008 70:1304. Epub 2007 Oct. 3.

The invention provides technical advantages, for example, the compound is novel and inhibits CGRP. Additionally, the compound provides advantages for pharmaceutical uses, for example, with regard to one or more of their mechanism of action, binding, inhibition efficacy, target selectivity, solubility, safety profiles, or bioavailability.

CGRP receptor antagonists have been disclosed in PCT publications including WO2003/104236.

DESCRIPTION OF THE INVENTION

The invention encompasses (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide (Compound I or the compound of formula I) and pharmaceutical compositions and methods for modulating CGRP and treating patients with medical conditions associated with aberrant levels of CGRP or CGRP receptor signaling.

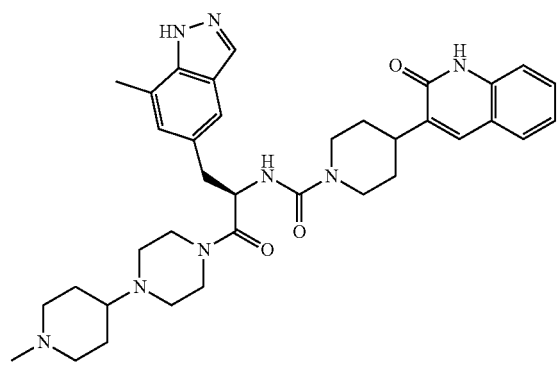

The invention includes all pharmaceutically acceptable salt forms of the compounds. Pharmaceutically acceptable salts are those in which the counter ions do not contribute significantly to the physiological activity or toxicity of the compounds and as such function as pharmacological equivalents. These salts can be made according to common organic techniques employing commercially available reagents. Some anionic salt forms include acetate, acistrate, besylate, bromide, chloride, citrate, fumarate, glucouronate, hydrobromide, hydrochloride, hydroiodide, iodide, lactate, maleate, mesylate, nitrate, pamoate, phosphate, succinate, sulfate, tartrate, tosylate, and xinofoate. Some cationic salt forms include ammonium, aluminum, benzathine, bismuth, calcium, choline, diethylamine, diethanolamine, lithium, magnesium, meglumine, 4-phenylcyclohexylamine, piperazine, potassium, sodium, tromethamine, and zinc.

The invention is intended to include all isotopes of atoms occurring in the present compounds. Isotopes include those atoms having the same atomic number but different mass numbers. By way of general example and without limitation, isotopes of hydrogen include deuterium and tritium. Isotopes of carbon include $^{13}C$ and $^{14}C$. Isotopically-labeled compounds of the invention can generally be prepared by conventional techniques known to those skilled in the art or by processes analogous to those described herein, using an appropriate isotopically-labeled reagent in place of the non-labeled reagent otherwise employed. Such compounds may have a variety of potential uses, for example as standards and reagents in determining biological activity. In the case of stable isotopes, such compounds may have the potential to favorably modify biological, pharmacological, or pharmacokinetic properties.

Synthetic Methods

Abbreviations generally follow conventions used in the art. Chemical abbreviations used in the specification and Examples are defined as follows: "NaHMDS" for sodium bis(trimethylsilyl)amide; "DMF" for N,N-dimethylformamide; "MeOH" for methanol; "NBS" for N-bromosuccinimide; "Ar" for aryl; "TFA" for trifluoroacetic acid; "LAH" for lithium aluminum hydride; "BOC", "DMSO" for dimethylsulfoxide; "h" for hours; "rt" for room temperature or retention time (context will dictate); "min" for minutes; "EtOAc" for ethyl acetate; "THF" for tetrahydrofuran; "EDTA" for ethylenediaminetetraacetic acid; "Et$_2$O" for diethyl ether; "DMAP" for 4-dimethylaminopyridine; "DCE" for 1,2-dichloroethane; "ACN" for acetonitrile; "DME" for 1,2-dimethoxyethane; "HOBt" for 1-hydroxybenzotriazole hydrate; "DIEA" for diisopropylethylamine, "Nf" for CF$_3$(CF$_2$)$_3$SO$_2$—; and "TMOF" for trimethylorthoformate.

Abbreviations as used herein, are defined as follows: "1×" for once, "2×" for twice, "3×" for thrice, "° C." for degrees Celsius, "eq" for equivalent or equivalents, "g" for gram or grams, "mg" for milligram or milligrams, "L" for liter or liters, "mL" or "ml" for milliliter or milliliters, "µL" for microliter or microliters, "N" for normal, "M" for molar, "mmol" for millimole or millimoles, "min" for minute or minutes, "h" for hour or hours, "rt" for room temperature, "RT" for retention time, "atm" for atmosphere, "psi" for pounds per square inch, "conc." for concentrate, "sat" or "sat'd" for saturated, "MW" for molecular weight, "mp" for melting point, "ee" for enantiomeric excess, "MS" or "Mass Spec" for mass spectrometry, "ESI" for electrospray ionization mass spectroscopy, "HR" for high resolution, "HRMS" for high resolution mass spectrometry, "LCMS" for liquid chromatography mass spectrometry, "HPLC" for high pressure liquid chromatography, "RP HPLC" for reverse phase HPLC, "TLC" or "tlc" for thin layer chromatography, "NMR" for nuclear magnetic resonance spectroscopy, "$^1$H" for proton, "δ" for delta, "s" for singlet, "d" for doublet, "t" for triplet, "q" for quartet, "m" for multiplet, "br" for broad, "Hz" for hertz, and "α", "β", "R", "S", "E", and "Z" are stereochemical designations familiar to one skilled in the art.

Compound I can be prepared according to Scheme 1. This synthesis is 14 chemical steps and highly convergent, coupling the three major fragments in the last three steps. As such, the synthesis begins with the preparation of major fragments A (Scheme 2) and B (Scheme 3).

Scheme 1

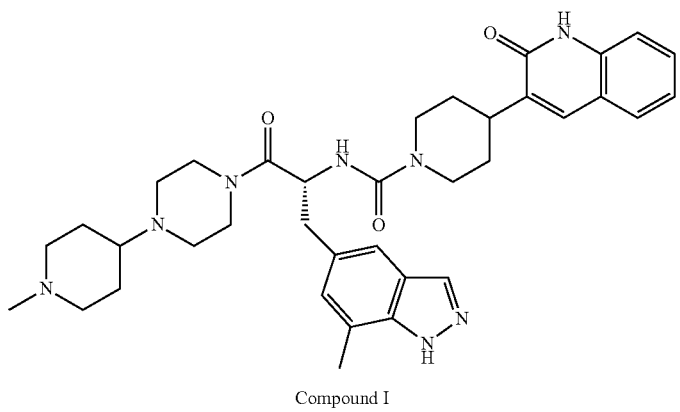

Compound I

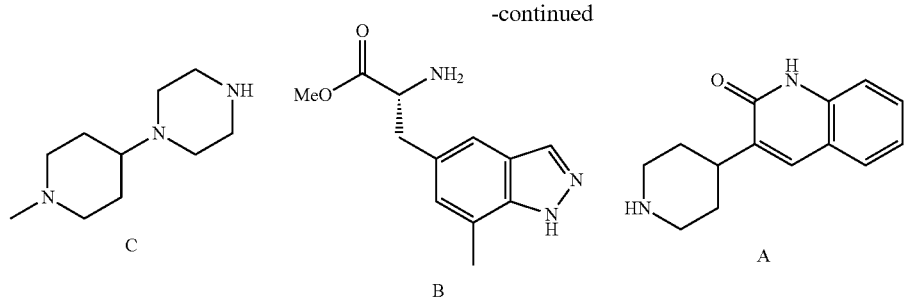

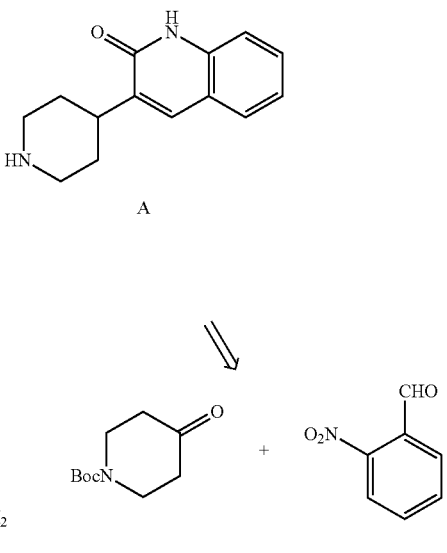

The synthesis of fragment A begins with Horner-Emmons reaction of N-Boc-4-piperidone with the ylide generated from trimethylphosphonoacetate to afford tert-butyl 4-(2-methoxy-2-oxoethylidene)piperidine-1-carboxylate in excellent yield (Scheme 2). Catalytic hydrogenation mediated by palladium on carbon reduces the unsaturated double bond. Treatment of tert-butyl 4-(2-methoxy-2-oxoethyl)piperidine-1-carboxylate with LDA generates the enolate which upon trapping with 2-nitrobenzaldehyde provides the nitro alcohol. Reduction of the nitro group with iron in acetic acid followed by treatment with hydrogen chloride in dioxane completes the synthesis of fragment A.

acetate in a Heck coupling to afford the product in 65% yield. At this point, the chiral center is installed using a catalytic asymmetric hydrogenation utilizing (−)-1,2-bis((2R,5R)-2,5-diethylphospholano)benzene(cyclooctadiene)rhodium(I) tetrafluoroborate and hydrogen (60 psi) to give the chiral amino acid in ~96% ee. The indazole ring is then formed by the action of iso-amyl nitrite. The resulting indazole is highly crystalline. One recrystallization from acetone/hexanes affords the indazole amino acid in excellent purity and with an improved 99.8% ee. Removal of the CBZ protecting group under hydrogenation conditions completes the preparation of fragment B. Indazole amino acid B can also be prepared using Scheme 2

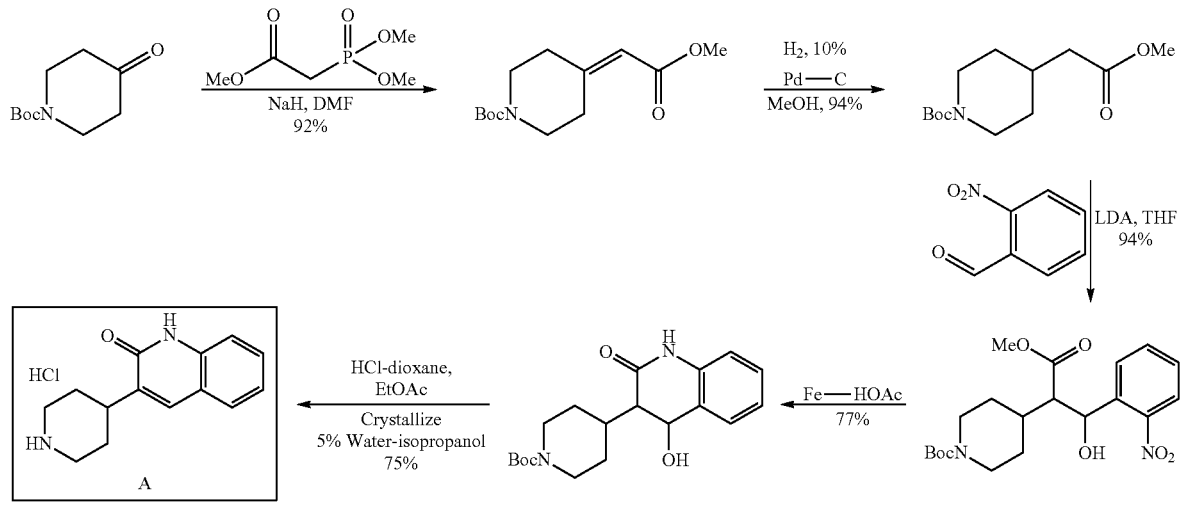

The synthesis of indazole amino acid B begins with the iodination of 2,6-dimethylaniline by the action of iodine monochloride (Scheme 3). This intermediate was temporarily set aside. N-CBZ-L-serine methyl ester undergoes a one-pot methanesulfonylation/elimination reaction to afford N-CBZ-dehydroalanine methyl ester. With the iodide and dehydroalanine in hand, they are efficiently coupled using palladium (II)

enzymatic resolution of the racemic amino acid or keto acid (Hanson, Ronald L.; Davis, Brian L.; Goldberg, Steven L.; Johnston, Robert M.; Parker, William L.; Tully, Thomas P.; Montana, Michael A.; Patel, Ramesh N. Process Research and Development, Bristol-Myers Squibb, New Brunswick, N.J., USA. Organic Process Research & Development (2008), 12(6), 1119-1129.).

Scheme 3

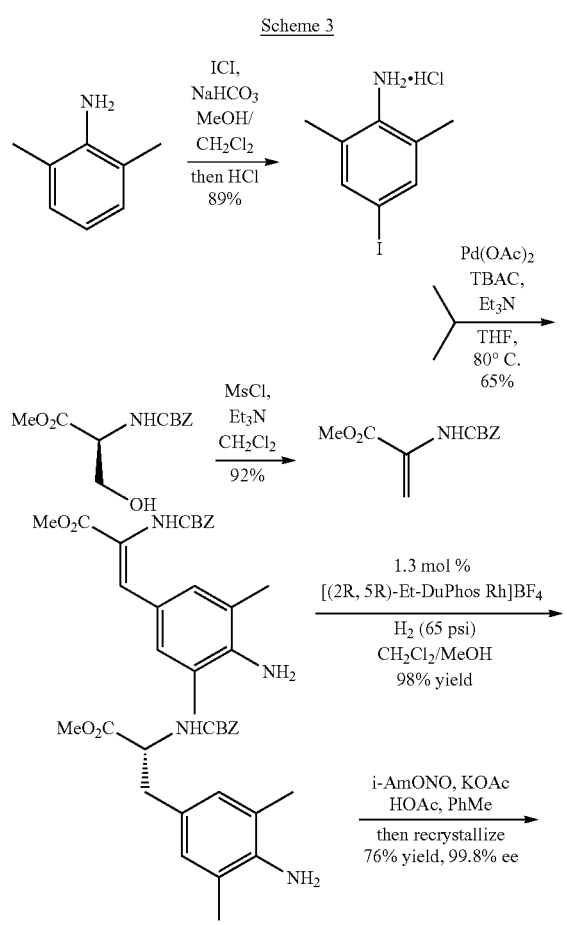

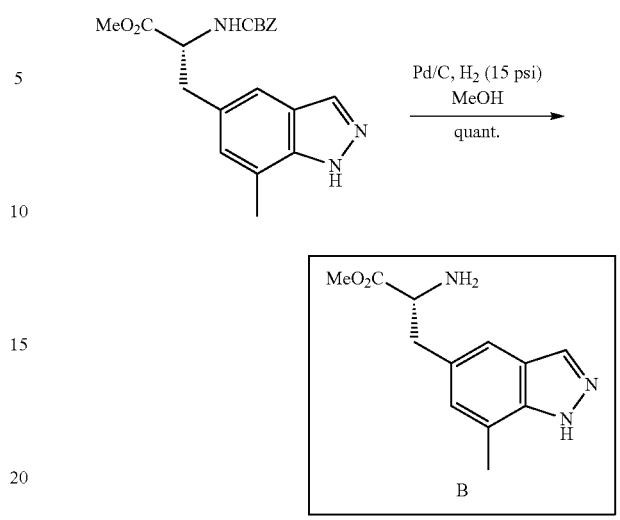

Fragments A and B are efficiently coupled using N,N'-disuccinimidyl carbonate to install the urea moiety in 78% yield (Scheme 4). Saponification of the methyl ester with lithium hydroxide gives a nearly quantitative yield of the carboxylic acid. TBTU® mediated coupling of acid with 1-(1-methylpiperidin-4-yl)piperazine completes the synthesis of Compound I. Flash chromatography affords the product as an amorphous powder which can be crystallized from acetone to afford Compound I as a fine white crystalline powder.

Scheme 4

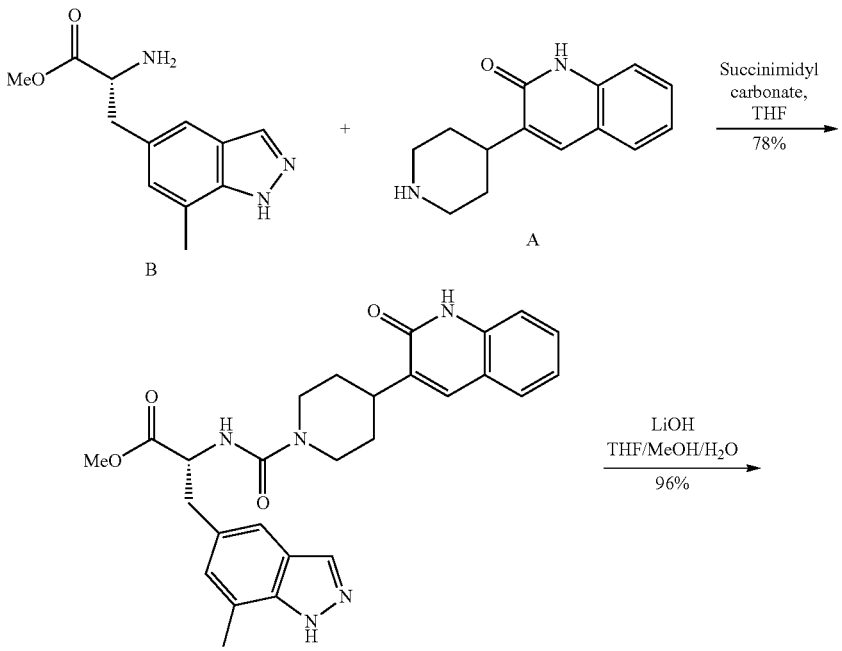

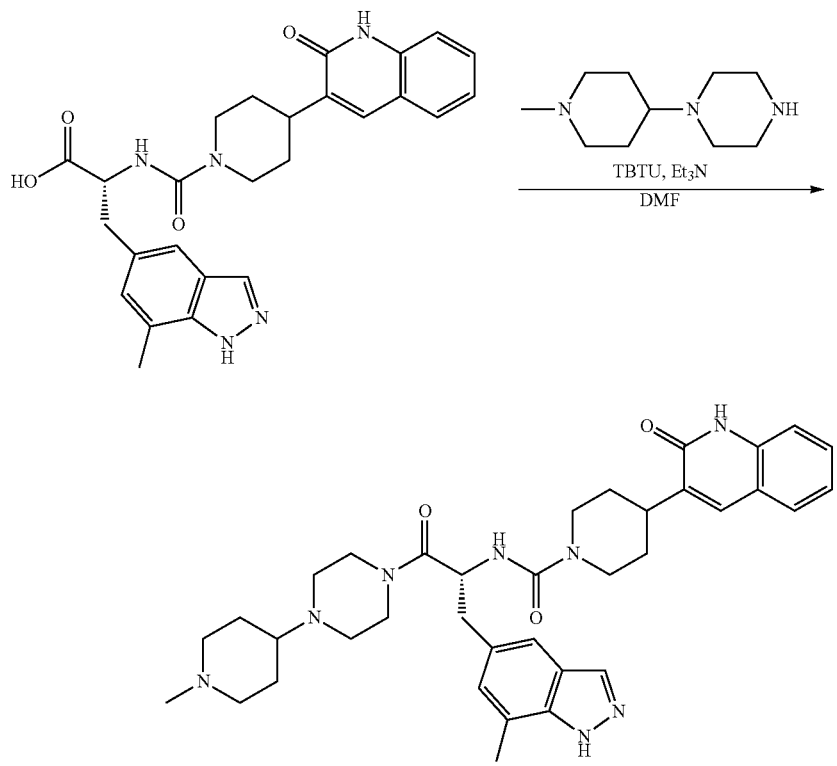

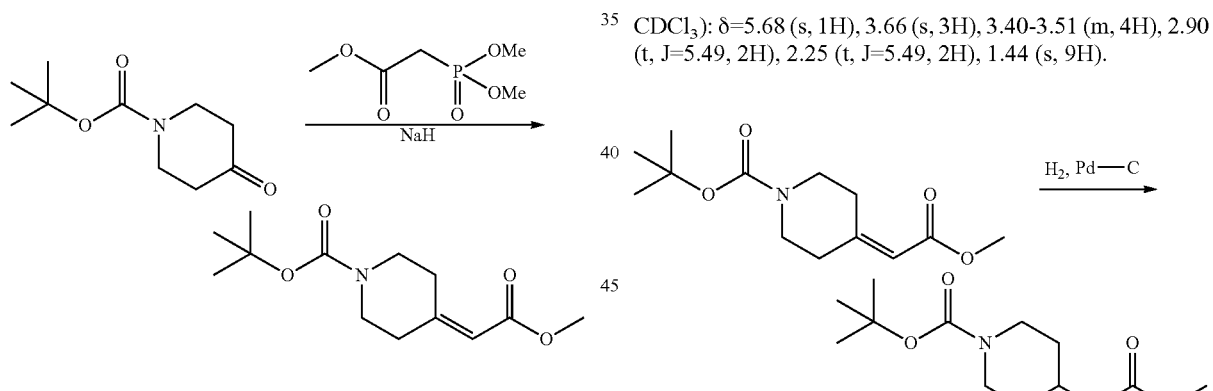

tert-butyl 4-(2-methoxy-2-oxoethylidene)piperidine-1-carboxylate.

Sodium hydride in mineral oil (60%, 7.92 g, 198.02 mmoles) was washed with hexanes then suspended in dimethylformamide (220 mL). The mixture was cooled to 0° C. Trimethyl phosphonoacetate (29.0 mL, 189.82 mmoles) was added dropwise to the stirred reaction mixture. After 20 min at 0° C., a solution of N-tert-butoxycarbonyl-4-piperidone (30.41 g, 152.62 mmoles) in dimethylformamide (80 mL) was added to the mixture dropwise. The reaction was stirred at room temperature for 3 h and then diluted with diethyl ether (650 mL). The mixture was washed once with water and the aqueous layer was extracted once with diethyl ether. The combined organic layers were washed 4 times with water and the aqueous phase was discarded. The organic phase was washed with brine and dried over magnesium sulfate, filtered, and concentrated to dryness. The title compound was obtained as a white solid in 92% yield. $^1$H-NMR (300 MHz, CDCl$_3$): δ=5.68 (s, 1H), 3.66 (s, 3H), 3.40-3.51 (m, 4H), 2.90 (t, J=5.49, 2H), 2.25 (t, J=5.49, 2H), 1.44 (s, 9H).

tert-butyl 4-(2-methoxy-2-oxoethyl)piperidine-1-carboxylate.

A solution of tert-butyl 4-(2-methoxy-2-oxoethylidene)piperidine-1-carboxylate (35.71 g, 140 mmoles) in a mixture of 1:1 ethyl acetate/methanol (220 mL) was carefully treated with 50% wet 10% palladium on carbon (3.3 g). The reaction vessel was charged with 55 psi of hydrogen gas and the mixture was shaken on a Parr apparatus at room temperature for 16 h. The reaction mixture was then filtered to remove the catalyst and the filtrate concentrated in vacuo. The title compound was obtained as a clear colorless oil in 97% yield. $^1$H-NMR (300 MHz, CDCl$_3$): δ=4.04 (d, J=10.25, 2H), 3.64 (s, 3H), 2.68 (t, J=12.44, 2H), 2.21 (d, J=6.95, 2H), 1.98-1.77 (m, 1H), 1.64 (d, J=13.54, 2H), 1.41 (s, 9H), 1.25-0.99 (m, 2H).

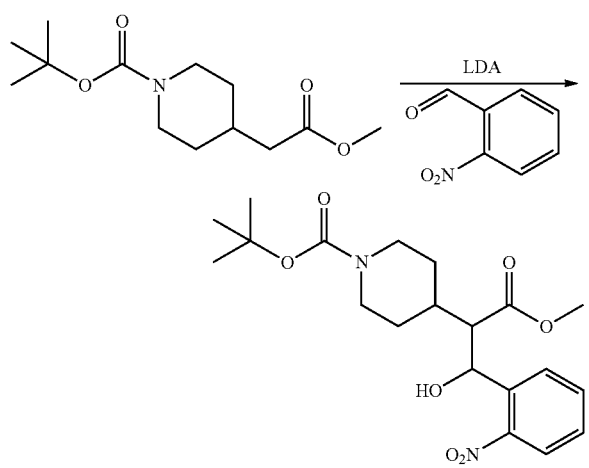

4-[2-Hydroxy-1-methoxycarbonyl-2-(2-nitro-phenyl)-ethyl]-piperidine-1-carboxylic acid tert-butyl ester.

N,N-diisopropylamine (4.40 mL, 31.3 mmoles) was dissolved in tetrahydrofuran (50 mL). The mixture was cooled to −78° C. Butyllithium (2.5 M in hexanes, 12.4 mL, 31 mmoles) was added dropwise to the stirred solution. After stirring at −78° C. for 30 min, a solution of tert-butyl 4-(2-methoxy-2-oxoethyl)piperidine-1-carboxylate (6.65 g, 25.8 mmoles) in tetrahydrofuran (15 mL) was added dropwise to the mixture. Stirring was continued at −78° C. for 1 h. A solution of 2-nitrobenzaldehyde (3.90 g, 25.8 mmoles) in tetrahydrofuran (20 mL) was then added to the mixture dropwise, and then stirring was continued at −78° C. for a further 2.5 h. The reaction was quenched with cold aqueous ammonium chloride and then diluted with water. The mixture was extracted twice with ethyl acetate and the aqueous phase was discarded. The material was dried (magnesium sulfate) filtered, and concentrated to dryness. Silica gel chromatography afforded the desired product in 94% yield as light yellow foam. MS m/e $(M-C_4H_8+H)^+=353.1$.

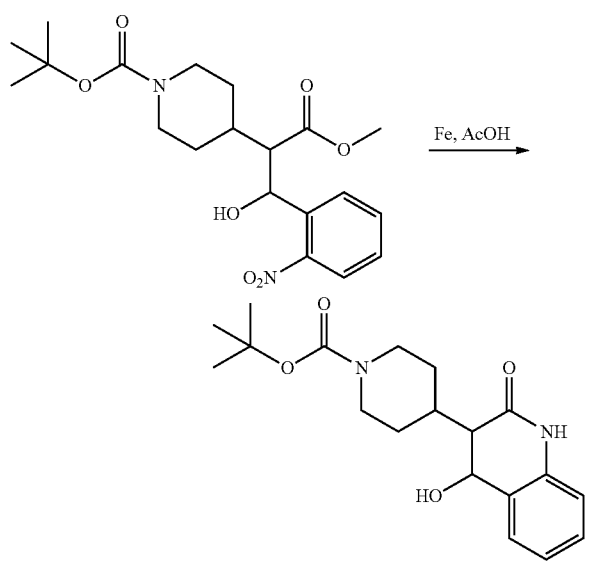

4-(4-Hydroxy-2-oxo-1,2,3,4-tetrahydro-quinolin-3-yl)-piperidine-1-carboxylic acid tert-butyl ester.

In a 3 neck flask fitted with a nitrogen inlet, thermometer, and a mechanical stirrer, 4-[2-hydroxy-1-methoxycarbonyl-2-(2-nitro-phenyl)-ethyl]-piperidine-1-carboxylic acid tert-butyl ester (9.93 g, 24.3 mmoles) was dissolved in acetic acid (1.75 moles, 100 mL). Iron powder (8.90 g, 159 mmoles) was added to the vessel with stirring. The stirred mixture was slowly heated to 80° C. for 30 min and then cooled to room temperature. It was then diluted with ethyl acetate and filtered through a pad of celite. Solids were washed with 20% methanol/ethyl acetate, and then with methanol. The filtrate was concentrated and the residue partitioned between ethyl acetate and aqueous sodium bicarbonate. The layers were separated. The resulting aqueous phase was extracted twice with ethyl acetate. The organic layers were combined. The mixture was washed twice with water and the aqueous phase was discarded. The material was dried (magnesium sulfate) filtered, and concentrated to dryness. Silica gel chromatography afforded the title compound as light yellow foam in 77% yield. MS m/e $(M-H)^-=345.1$.

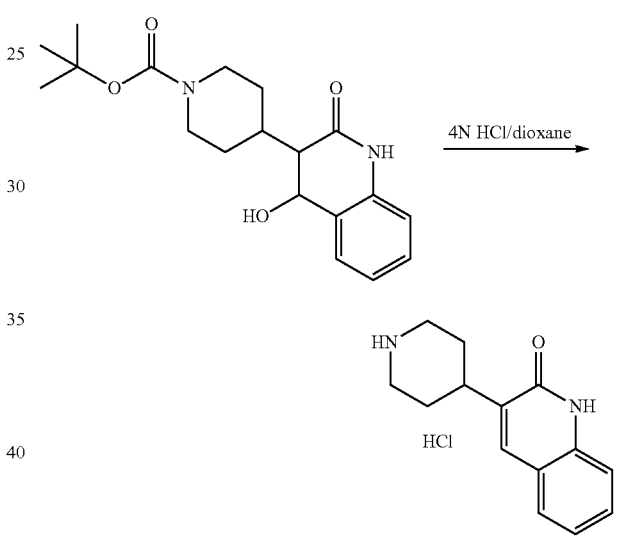

3-(Piperidin-4-yl)quinolin-2(1H) hydrochloride.

A stirred solution of 4-(4-hydroxy-2-oxo-1,2,3,4-tetrahydro-quinolin-3-yl)-piperidine-1-carboxylic acid tert-butyl ester (5.60 g, 16.2 mmoles) in ethyl acetate (70 mL) was treated with HCl in dioxane (4N, 40 mmoles, 10 mL). The mixture was stirred at room temperature for 45 min. More HCl in dioxane (4N, 120 mmoles, 30 mL) was then added and stirring was continued at room temperature for 16 h. The resulting solid was collected by filtration and washed with ethyl acetate. It was then suspended in 5% water-isopropanol (100 mL) and the mixture was warmed to reflux and stirred for 20 min. The mixture was cooled to room temperature and stirred at room temperature for 16 h. The solid was collected by filtration, washed with isopropanol, and dried under high vacuum. The title compound was obtained as white solid in 75% yield. $^1$H-NMR (DMSO-$d_6$) δ 11.85 (s, 1H), 9.02 (bs, 1H), 8.88 (bs, 1H), 7.70 (t, J=3.81 Hz, 2H), 7.53-7.30 (d, J=8.24 Hz, 1H), 7.17 (t, J=7.48 Hz, 2H), 3.36 (d, J=12.51 Hz, 2H), 3.10-2.94 (m, 3H), 2.01 (d, J=13.43 Hz, 2H), 1.87-1.73 (m, 2H); MS m/e $(M+H)^+=229.0$.

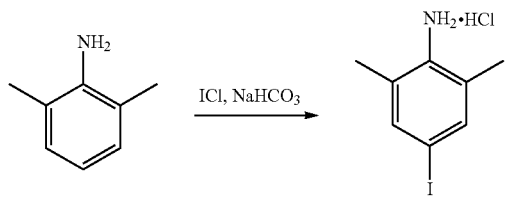

4-Iodo-2,6-dimethylbenzenamine hydrochloride.

To a suspension of sodium bicarbonate (126 g, 1.5 moles) and 2,6-dimethylaniline (61.5 mL, 500 mmoles) in methanol (700 mL) was added iodine monochloride (1.0 M in dichloromethane, 550 mL, 550 mmoles) at room temperature over 1 h. After addition was complete, stirring was continued for 3 h. The reaction was filtered to remove excess sodium bicarbonate and the solvent removed in vacuo. The residue was redissolved in diethyl ether (1.5 L) and treated with hydrochloric acid (2M in ether, 375 mL, 750 mmoles). The resulting suspension was stored in the freezer (−15° C.) overnight. The solid was filtered and washed with diethyl ether until it became colorless, to give 126.5 g (89%) as a grey-green powder. $^1$H-NMR (DMSO-d$_6$) δ 2.33 (s, 6H), 7.48 (s, 2H), 9.05 (bs, 3H); $^{13}$C-NMR (DMSO-d$_6$) δ 17.4, 91.5, 133.1, 131.2, 136.9.

Methyl 2-(benzyloxycarbonyl)acrylate.

To a flame dried three-neck round bottom flask, fitted with a mechanical stirrer, was added (S)-methyl 2-(benzyloxycarbonyl)-3-hydroxypropanoate (129 g, 509 mmoles), anhydrous dichloromethane (2 L), and methanesulfonyl chloride (49.3 mL, 636 mmoles). The mixture was cooled to −15° C., and treated with triethylamine (213 mL, 1527 mmoles), dropwise, to ensure the temperature of the reaction mixture did not exceed 0° C. The addition of the first equivalent of triethylamine was exothermic. After addition of triethylamine, the mixture was stirred at 0° C. for 30 min. The cooling bath was removed and the mixture stirred at room temperature for 1.5 h. The reaction was quenched by addition of methanol (21 mL). The mixture was washed with 0.5% aqueous potassium bisulfate until the washings were pH 5, then saturated sodium bicarbonate, and brine, dried over sodium sulfate, and concentrated. Flash chromatography (silica gel, 1:9 ethyl acetate/hexanes) gave 111 g (92%) as a viscous colorless oil, which crystallized upon standing. $^1$H-NMR (DMSO-d$_6$) δ 3.71 (s, 3H), 5.10 (s, 2H), 5.60 (s, 1H), 5.76 (s, 1H), 7.39-7.35 (m, 5H), 8.96 (s, 1H); $^{13}$C-NMR (DMSO-d$_6$) δ 52.3, 65.9, 127.8, 128.1, 128.3, 128.8, 133.3, 136.3, 153.5, 163.7.

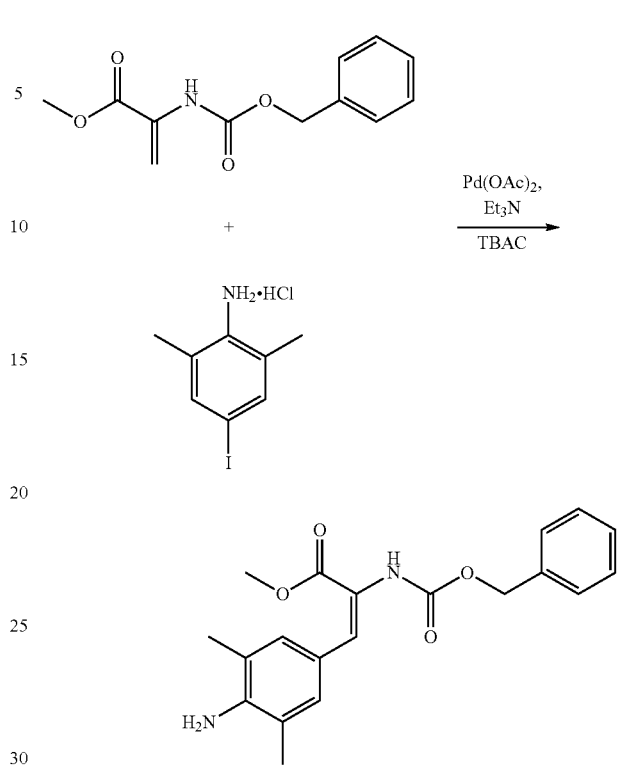

(Z)-Methyl 3-(4-amino-3,5-dimethylphenyl)-2-(benzyloxycarbonyl)acrylate.

A 2 L round bottom flask was charged 4-iodo-2,6-dimethylbenzenamine hydrochloride salt (55 g, 194 mmoles), methyl 2-(benzyloxycarbonyl)acrylate (59.2 g, 252 mmoles), tetrabutylammonium chloride (59.2 g, 213 mmoles), palladium (II) acetate (4.34 g, 19.4 mmoles), and tetrahydrofuran (1.2 L, degassed by a flow of nitrogen for 30 min). The mixture was stirred so that a suspension was formed and then degassed by a flow of nitrogen for 30 min. Triethylamine (110 mL, 789 mmoles) was added and the resulting mixture was heated at reflux for 3 h. After cooling to room temperature, the reaction mixture was filtered through a pad of celite, washed with tetrahydrofuran (2×100 mL), and concentrated. The residue was dissolved in dichloromethane, washed with water (3×) and brine (2×), dried over sodium sulfate, and concentrated. Flash chromatography (silica gel, using 1:9 ethyl acetate/dichloromethane) gave a tan solid. The solid was recrystallized from warm methanol (210 mL) and water (100 mL). The mixture was held at room temperature overnight, then at 0° C. for 2 h, and finally at −15° C. for 2 h. The resulting solid was filtered, washed with ice cold 1:1 methanol/water, and dried under high vacuum overnight to give 44.7 g (65%) as a light tan solid which was a mixture of Z/E isomers (73:27). $^1$H-NMR (DMSO-d$_6$) 6, 2.05 (s, 6H), 3.61 (s, 0.8H), 3.68 (s, 2.2H), 5.00 (s, 0.54H), 5.13 (s, 1.46H), 5.24 (s, 2H), 7.40-7.21 (m, 8H), 8.51 (s, 0.27 H), 8.79 (s, 0.73H); $^{13}$C-NMR (DMSO-d$_6$) δ 17.8, 51.7, 65.3, 119.4, 120.0, 120.3, 127.3, 127.7, 128.3, 130.9, 135.8, 137.2, 146.9, 154.7, 166.0.

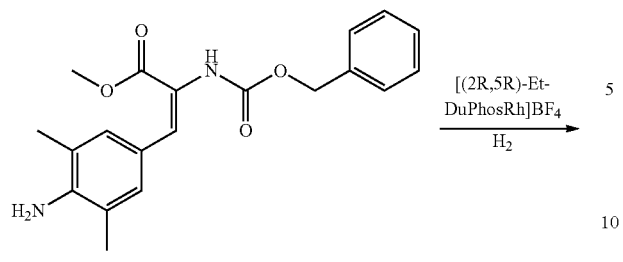

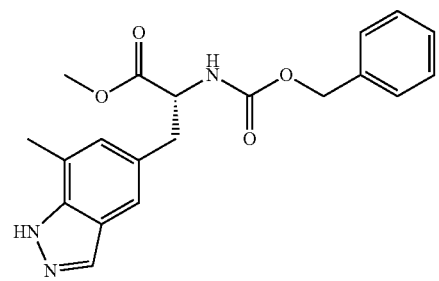

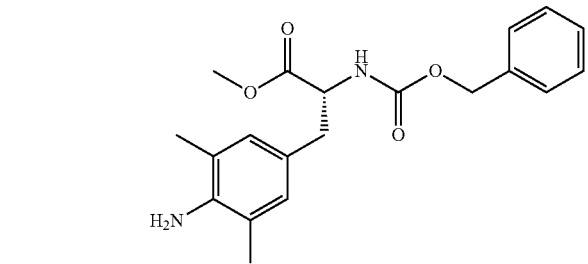

(R)-Methyl 3-(4-amino-3,5-dimethylphenyl)-2-(benzyloxycarbonyl)propanoate.

A flame-dried 2 L Parr hydrogenation bottle was charged with (Z)-methyl 3-(4-amino-3,5-dimethylphenyl)-2-(benzyloxycarbonyl)acrylate (84.5 g, 239 mmoles), dichloromethane (300 mL), and methanol (300 mL). The bottle was swirled so that a light brown suspension was formed. The mixture was degassed using a flow of nitrogen for 30 min. To this was quickly added (−)-1,2-bis((2R,5R)-2,5-diethylphospholano)-benzene(cyclooctadiene) rhodium (I) tetrafluoroborate ([(2R,5R)-Et-DuPhosRh]BF$_4$) (2.11 g, 3.20 mmoles). The bottle was immediately attached to a Parr Hydrogenator. After 5 cycles of hydrogen (60 psi) and vacuum, the bottle was pressurized to 65 psi and the suspension was agitated at room temperature for 16 h. The reaction had become homogeneous. The reaction mixture was concentrated, and the resulting residue purified by flash chromatography (silica gel, 1:9 ethyl acetate/dichloromethane) to give 82.9 g (98%). $^1$H-NMR (DMSO-d$_6$) δ 2.04 (s, 6H), 2.65 (dd, J=13.4, 9.8 Hz, 1H), 2.82 (dd, J=13.7, 5.2Hz, 1H), 3.62 (s, 3H), 4.15-4.10 (m, 1H), 4.41 (s, 2H), 5.00 (s, 2H), 6.68 (s, 2H), 7.37-7.28 (m, 5H), 7.70 (d, J=7.9 Hz, 1H); $^{13}$C-NMR (DMSO-d$_6$) δ 17.7, 35.9, 51.7, 56.1, 65.3, 120.4, 124.0, 127.5, 127.7, 128.2, 128.3, 136.9, 142.6, 155.9, 172.5.

(R)-Methyl 2-(benzyloxycarbonyl)-3-(7-methyl-1H-indazol-5-yl)propanoate.

(R)-Methyl 3-(4-amino-3,5-dimethylphenyl)-2-(benzyloxycarbonyl)propanoate (50.0 g, 140 mmoles) was weighed into a flame-dried 5 L three neck round bottom flask, followed by the addition of toluene (2.4 L) and glacial acetic acid (120 mL, 2.1 moles). The mixture was mechanically stirred to form a clear solution, and then potassium acetate (103 g, 1.05 moles) was added. To the resulting white suspension, isoamyl nitrite (20.7 mL, 154 mmoles) was added dropwise at room temperature, and the resulting mixture was stirred at room temperature for 16 h. Saturated sodium bicarbonate (1 L) was added, followed by the careful addition of solid sodium bicarbonate to neutralize the acetic acid. The mixture was extracted with a mixture of dichloromethane (2 L) and brine (1.5 L). After separation, the aqueous layer was extracted with dichloromethane (500 mL). The combined organic layers were dried over anhydrous sodium sulfate and filtered. Solvents were removed to afford a tan solid, which was washed with hexanes (2 L) and toluene (150 mL). The solid was recrystallized from hot acetone (260 mL) and hexanes (700 mL). The slightly cloudy mixture was allowed to cool to room temperature slowly, then to 0° C. for 1.5 h, and finally to −15° C. for 1.5 h. The resulting solid was filtered and washed with ice-cold acetone/hexanes (1:1, 200 mL) to afford 39.1 g (76% yield). Analytical HPLC showed >98% UV purity. The enantiomeric excess (ee) was determined to be 99.8% (conditions: Chiralpak AD column, 4.6×250 mm, 10 µm; A=ethanol, B=0.05% diethylamine/heptane; 85% B @1.0 mL/min. for 55 min. The retention times for R was 44.6 min and for S was 28.8 min) $^1$H-NMR (DMSO-d$_6$) δ 2.48 (s, 3H), 2.93 (dd, J=13.4, 10.7 Hz, 1H), 3.10 (dd, J=13.7, 4.9 Hz, 1H), 3.63 (s, 3H), 4.32-4.27 (m, 1H), 4.97 (s, 2H), 7.03 (s, 1H), 7.24-7.22 (m, 2H), 7.29-7.27 (m, 3H), 7.41 (s, 1H), 7.83 (d, J=8.2Hz, 1H), 7.99 (s, 1H), 13.1 (s, 1H); $^{13}$C-NMR (DMSO-d$_6$) δ 16.7, 36.5, 51.8, 56.0, 65.3, 117.6, 119.6, 122.7, 127.2, 127.4, 127.6, 128.2, 129.3, 133.4, 136.8, 139.2, 155.9, 172.4. Mass spec.: 368.16 (MH)$^+$.

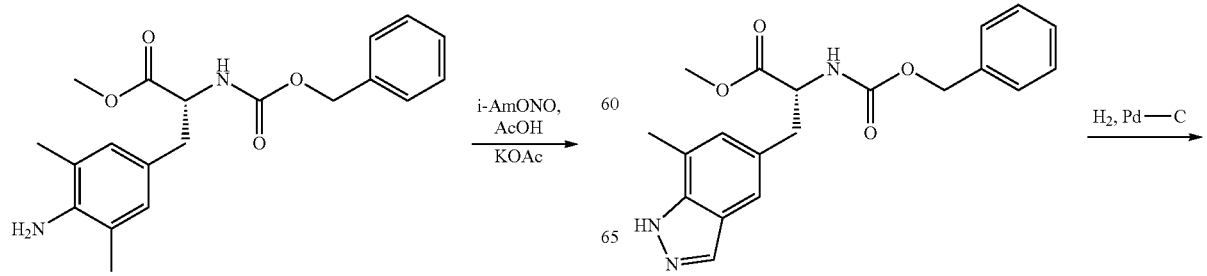

-continued

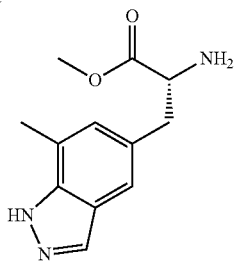

(R)-Methyl 2-amino-3-(7-methyl-1H-indazol-5-yl)propanoate.

A Parr hydrogenation bottle was charged with (R)-methyl 2-(benzyloxycarbonyl)-3-(7-methyl-1H-indazol-5-yl)propanoate (11.0 g, 29.9 mmoles) and methanol (75 mL). The suspension was purged with nitrogen and treated with palladium (10% on charcoal, 700 mg). The bottle was shaken under hydrogen (15 psi) overnight. The mixture was filtered through a pad of celite to remove the catalyst. Concentration of the eluent gave 7.7 g (quant.) as an oil which was used without further purification. $^1$H-NMR (CD$_3$OD) δ 2.54 (s, 3H), 2.98 (dd, J=13.5, 7.0 Hz, 1H), 3.09 (dd, J=13.5, 5.9 Hz, 1H), 3.68 (s, 3H), 3.75 (dd, J=7.0, 6.2Hz, 1H), 7.01 (s, 1H), 7.39 (s, 1H), 7.98 (s, 1H). Mass spec.: 232.34 (M−H)$^−$.

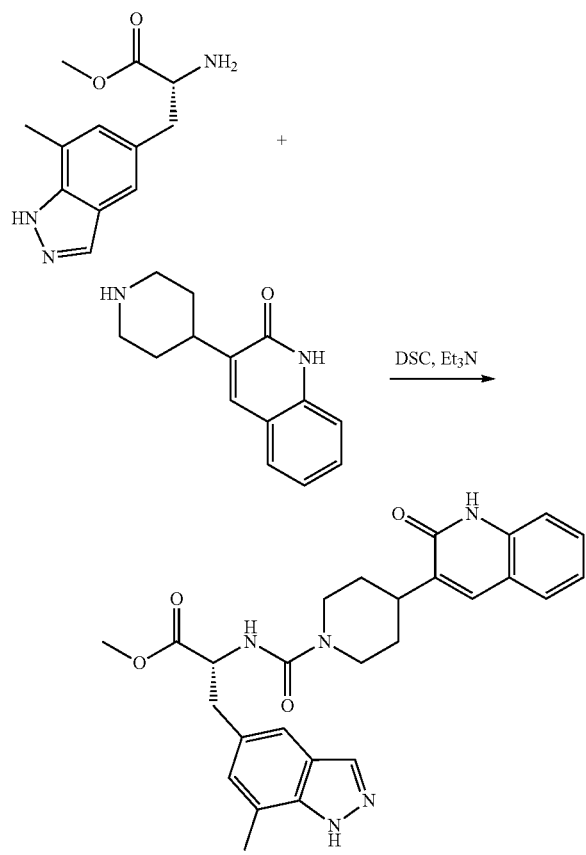

(R)-methyl 3-(7-methyl-1H-indazol-5-yl)-2-(4-(2-oxo-1,2-dihydroquinolin-3-yl)piperidine-1-carboxamido)propanoate.

To a solution of (R)-methyl 2-amino-3-(7-methyl-1H-indazol-5-yl)propanoate hydrochloride (7.26 g, 27.0 mmoles) in dimethylformamide (50 mL) at room temperature was added N,N'-disuccinimidyl carbonate (7.60 g, 29.7 mmoles) followed by triethylamine (11.29 mL, 81 mmoles). The resulting mixture was stirred for 30 min and treated with 3-(piperidin-4-yl)quinolin-2(1H)-one (6.77 g, 29.9 mmoles) in portions. The reaction was allowed to stir for 24 h. The mixture was concentrated, dissolved in ethyl acetate, and washed sequentially with water, brine, and 0.5 N HCl (2×). The organic phase was dried over magnesium sulfate, filtered, and concentrated. The resulting residue was purified by flash chromatography (silica gel, 20:1 ethyl acetate/methanol) to give 11.9 g (78%). $^1$H-NMR (CD$_3$OD) δ 13.0 (s, 1H), 11.8 (s, 1H), 7.98 (s, 1H), 7.63 (d, J=7.6 Hz, 1H), 7.57 (s, 1H), 7.45-7.41 (m, 2H), 7.27 (d, J=8.2Hz, 1H), 7.16 (t, J=7.9 Hz, 1H), 7.03 (s, 1H), 6.85 (d, J=7.9 Hz, 1H), 4.31-4.26 (m, 1H), 4.10-4.08 (m, 2H), 3.60 (s, 3H), 3.07-3.01 (m, 2H), 2.93-2.88 (m, 1H), 2.77-2.67 (m, 2H), 2.48 (s, 3H), 1.78-1.72 (m, 2H), 1.34-1.26 (m, 2H). Mass spec.: 488.52 (MH)$^+$.

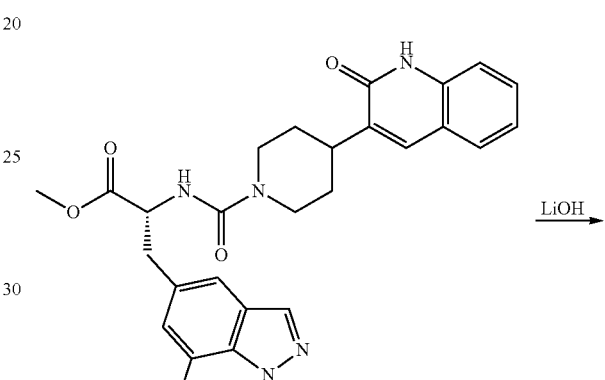

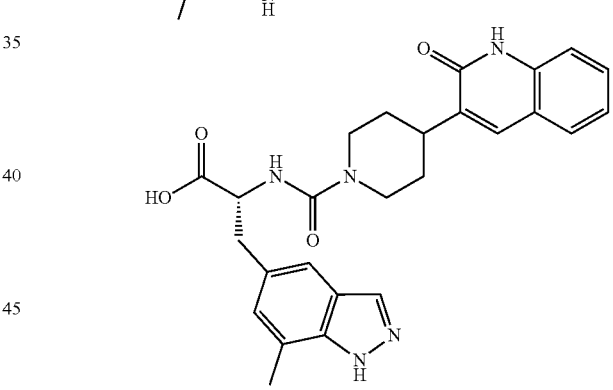

(R)-3-(7-methyl-1H-indazol-5-yl)-2-(4-(2-oxo-1,2-dihydroquinolin-3-yl)piperidine-1-carboxamido)propanoic acid.

A solution of (R)-methyl 3-(7-methyl-1H-indazol-5-yl)-2-(4-(2-oxo-1,2-dihydroquinolin-3-yl)piperidine-1-carboxamido)propanoate (5.50 g, 11.3 mmoles) in tetrahydrofuran (50 mL) and methanol (10 mL) was cooled to 0° C. To this was added a cold (0° C.) solution of lithium hydroxide monohydrate (0.95 g, 22.6 mmoles) in water (20 mL), dropwise over 15 min. The reaction was stirred at room temperature for additional 3 h. The mixture was concentrated to remove the organic solvents. The resulting residue was dissolved in a minimum amount of water, cooled to 0° C., and treated with cold (0° C.) 1N HCl until pH 2 was attained. The resulting solid was collected by filtration, washed with cold water and ether, and then dried overnight under high vacuum to give 5.0 g (94%) as a white solid. $^1$H-NMR (DMSO-d$_6$) δ 13.05 (bs, 1H), 11.77 (s, 1H), 7.98 (s, 1H), 7.62 (d, J=8.0 Hz, 1H), 7.55 (s, 1H), 7.44 (d, J=8.2Hz, 1H), 7.42 (s, 1H), 7.27 (d, J=8.2Hz, 1H), 7.16 (t, J=7.6 Hz, 1H), 7.05 (s, 1H), 6.65 (d, J=7.9 Hz, 1H), 4.27-4.22 (m, 1H), 4.10-4.07 (m, 2H), 3.12-3.07 (m, 1H), 3.03-2.99 (m, 1H), 2.93-2.88 (m, 1H), 2.77-2.66 (m, 2H), 2.47 (s, 3H), 1.77-1.74 (m, 2H), 1.34-1.27 (m, 2H). Mass spec.: 474.30 (MH)+.

1H), 3.11 (m, 1H), 2.97 (m, 1H), 2.89 (m, 2H), 2.69 (m, 4H), 2.32 (m, 1H), 2.21 (m, 1H), 2.07 (m, 4H), 1.95 (t, J=8.25 Hz, 1H), 1.87 (m, J=11.28, 11.28, 3.55, 3.44 Hz, 1H), 1.76 (t, J=12.03 Hz, 2H), 1.68 (t, J=11.11 Hz, 2H), 1.53 (t, J=8.25 Hz, 1H), 1.32 (m, 4H), 1.16 (m, 2H); $^{13}$C-NMR (DMSO-$d_6$) δ 16.80, 27.30, 30.51, 30.51, 30.67, 35.50, 38.04, 41.74, 44.00, 44.16, 45.35, 45.78, 48.14, 48.39, 51.45, 54.76, 54.76, 60.61, 114.53, 117.79, 119.29, 119.34, 121.57, 122.78, 127.46, 127.79, 129.29, 129.79, 133.31, 133.72, 136.98, 137.41, 139.12, 156.50, 161.50, 170.42. Accurate mass analysis: m/z 639.3770, [MH]+, Δ=−0.2 ppm. Optical rotation: −27.36° @ 589 nm, concentration=4.71 mg/mL in methanol.

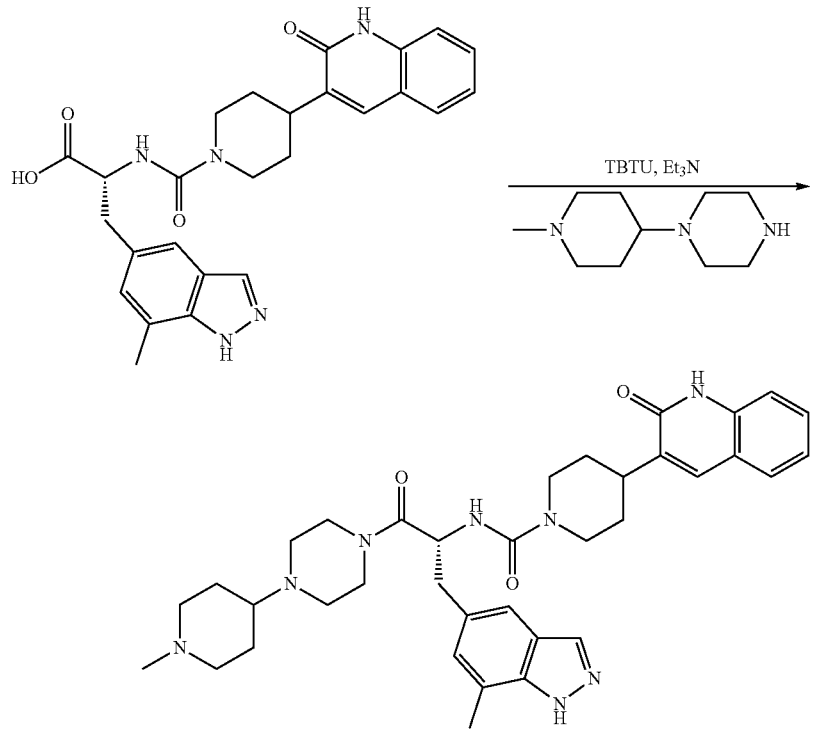

(R)—N-(3-(7-methyl-1H-indazol-5-yl-1-(4-(1-methylpiperidin-4-yl)piperazin-1-yl)-1-oxopropan-2-yl)-4-(2-oxo-1,2-dihydroquinolin-3-yl)piperidine-1-carboxamide (I).

A flask was charged with (R)-3-(7-methyl-1H-indazol-5-yl)-2-(4-(2-oxo-1,2-dihydroquinolin-3-yl)piperidine-1-carboxamido)propanoic acid (2.9 g, 6.11 mmoles), triethylamine (3.00 mL, 21.5 mmoles), 1-(1-methylpiperidin-4-yl)piperazine (1.23 g, 6.72 mmoles), and dimethylformamide (10 mL). The resulting solution was treated with 2-(1H-benzotriazole-1-yl)-1,1,3,3-tetramethyluronium tetrafluoroborate (2.26 g, 7.03 mmoles) in portions. The reaction was allowed to stir at room temperature overnight. The mixture was concentrated under vacuum to remove dimethylformamide. The crude product was dissolved in 7% methanol in dichloromethane and purified by flash chromatography using 7% methanol in dichloromethane containing 2% of aqueous ammonium hydroxide as eluent. The pure fractions were collected and solvent was removed under vacuum. The desired product was crystallized from hot acetone to give Compound I in 77% yield. Analytical HPLC showed 99.0% UV purity at 230 nm. The enantiomeric excess (ee) was determined to be >99.9% (conditions: Chiralpak AD column, 4.6×250 mm, 10 μm; eluent: 70% (0.05% diethylamine)/heptane/30% ethanol; @1.0 mL/min. for 45 min. The retention times were 18.7 min for R and 28.1 min for S). $^1$H-NMR (500 MHz, DMSO-$d_6$) δ ppm 13.01 (s, 1H), 11.76 (s, 1H), 7.96 (s, 1H), 7.62 (d, J=7.10 Hz, 1H), 7.60 (s, 1H), 7.42 (m, 1H), 7.36 (s, 1H), 7.26 (d, J=8.25 Hz, 1H), 7.14 (m, 1H), 7.00 (s, 1H), 6.69 (d, J=8.25 Hz, 1H), 4.78 (q, J=7.79 Hz, 1H), 4.14 (d, J=12.37 Hz, 2H), 3.54 (dd, J=9.16, 4.58 Hz, 1H), 3.24 (m, Biological Methods and Other Properties Scheme 5. Compound I and comparator compounds II and III.

I

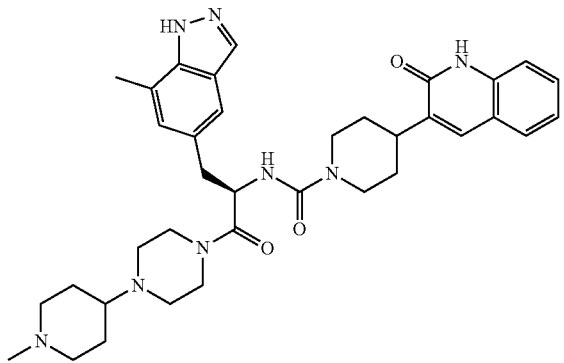 [SMILES: Cc1cc(C[C@@H](NC(=O)N2CCC(c3cc4ccccc4[nH]c3=O)CC2)C(=O)N2CCN(C3CCN(C)CC3)CC2)cc2cn[nH]c12]

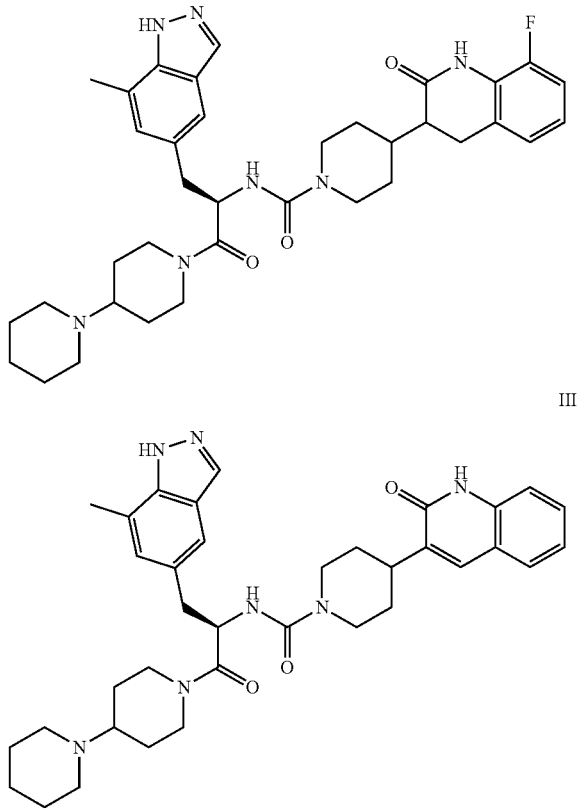

Aqueous Solubility.

Solid free base was mixed with carbonate, and ethanolamine buffers. The pH of a third sample was adjusted with HCl. The solids were mixed with the vehicles using a mixer that was enclosed within an incubator set to 25 C. After equilibration, samples of the supernatant were withdrawn, diluted as appropriate, and analyzed by HPLC.

Solubility in Aqueous Media, pH Dependence.

Crystalline Compound I converted to a gelatinous phase during measurement of the pH solubility profile. The absence of a crystalline phase in equilibrium with water prevents a confident assessment of the pH range in which Compound I can be formulated as a thermodynamically stable solution. Efforts to generate a crystalline free base form of Compound I that can be equilibrated in water are ongoing. The data gathered on the gelatinous phase are listed in Table 1.

TABLE 1

Solubility of Compound I in aqueous media at 25 C.

| Vehicle | Solubility (mg/mL) |
|---|---|
| Carbonate buffer, pH = 10.4 | .2 |
| Ethanolamine buffer, pH = 9.4 | .5 |
| Partial titration of Compound I with HCl, pH = 8.5 | 105 |
| pH < 8.5 | >300 |

Solution State Stability.

The solution state stability of Compound I was evaluated as a function of temperature, pH, high intensity light (HIL), buffer concentration, and drug concentration. The experimental matrix used is shown in Table 2.

TABLE 2

Solution State Stability Matrix

| Sample | pH | Temp (C.) | Drug Conc (mg/ml) | Buffer Conc. (M) |
|---|---|---|---|---|
| A | 4 | 40 | 0.1 | 0.05 |
| B | 5 | 25 | 0.1 | 0.05 |
| C | 5 | 25/light | 0.1 | 0.05 |
| D | 5 | 60 | 0.1 | 0.05 |
| E | 5 | 40 | 0.1 | 0.05 |
| F | 6 | 40 | 0.1 | 0.05 |
| G | 4 | 40 | 40 | 0.05 |
| H | 5 | 40 | 40 | 0.05 |
| I | 6 | 40 | 40 | 0.05 |
| J | 5 | 40 | 0.1 | 0.01 |

Succinate buffer was used for all solutions. For samples exposed to light, a photostability chamber was used in accordance with ICH guidelines (1.2 million lux hour exposure to visible light and 200 watt hour/m$^2$ to UV). Analyses were performed at 4, 8 and 12 weeks.

Ten degradants were found during the solution stability study. The percentage of each degradant found in samples after 12 weeks of storage is listed in Table 3. Note that at the initial time point, degradants B and G were the only degradants present and their initial concentrations were 0.17% and 0.06% respectively.

Mass spectroscopic assessment was performed on those degradants present in sufficient quantity to permit a mass determination. The results are listed in Table 4. Two peaks are listed under degradant B, because it was discovered that two degradants are not well separated by the current HPLC method. Degradants A and C correspond to hydrolysis products (FIG. 2).

Under the most favorable condition examined, condition I in Table 2, Compound I showed only 0.3% degradation after 12 weeks at 40 C. This suggests that an aqueous formulation can be found which meets ICH guidelines for at least one year of chemical stability.

TABLE 3

Area percent of degradants seen at twelve weeks and their retention times (minutes)

| | Deg A $t_r = 3.9$ | Deg B $t_r = 5.4$ | Deg C $t_r = 4.6$ | Deg D $t_r = 4.1$ | Deg E $t_r = 5.0$ | Deg F $t_r = 6.6$ | Deg G $t_r = 7.5$ | Deg H $t_r = 6.7$ | Deg I $t_r = 4.3$ | Deg J $t_r = 5.6$ |
|---|---|---|---|---|---|---|---|---|---|---|
| A | 2.0 | — | 10.5 | — | — | — | — | — | — | — |
| B | .5 | 0.1 | — | — | — | — | — | — | — | — |
| C | 16.9 | 2.9 | 2.8 | 5.2 | 1.0 | 7.7 | — | — | 5.7 | — |
| D | 1.2 | — | 55.0 | — | — | — | — | — | — | — |
| E | 1.9 | 0.2 | — | — | .1 | — | — | — | — | — |
| F | .4 | 0.1 | — | — | .1 | — | — | — | — | — |
| G | 4.9 | — | — | — | 3.5 | — | 0.1 | .1 | — | 0.1 |
| H | 1.2 | 0.1 | — | — | 0.0 | — | 0.1 | — | — | 0.0 |

TABLE 3-continued

Area percent of degradants seen at twelve weeks and their retention times (minutes)

| | Deg A $t_r = 3.9$ | Deg B $t_r = 5.4$ | Deg C $t_r = 4.6$ | Deg D $t_r = 4.1$ | Deg E $t_r = 5.0$ | Deg F $t_r = 6.6$ | Deg G $t_r = 7.5$ | Deg H $t_r = 6.7$ | Deg I $t_r = 4.3$ | Deg J $t_r = 5.6$ |
|---|---|---|---|---|---|---|---|---|---|---|
| I | .2 | 0.1 | 0.0 | — | 0.0 | — | 0.1 | — | — | 0.1 |
| J | 1.1 | 0.1 | — | — | .1 | — | — | 0.5 | — | — |

TABLE 4

Degradant Molecular Weights

| Degradant Label | Molecular Weight |
|---|---|
| A | 473.5 |
| B | 541.4 |
| | 612.4 |
| C | 228.3 |

TABLE 5

Solution Stability and Temperature

| pH | Total Degradants (25 C.) | Total Degradants (40 C.) | Total Degradants (60 C.) |
|---|---|---|---|
| 5 | .6% | 2.2% | 56.2% |

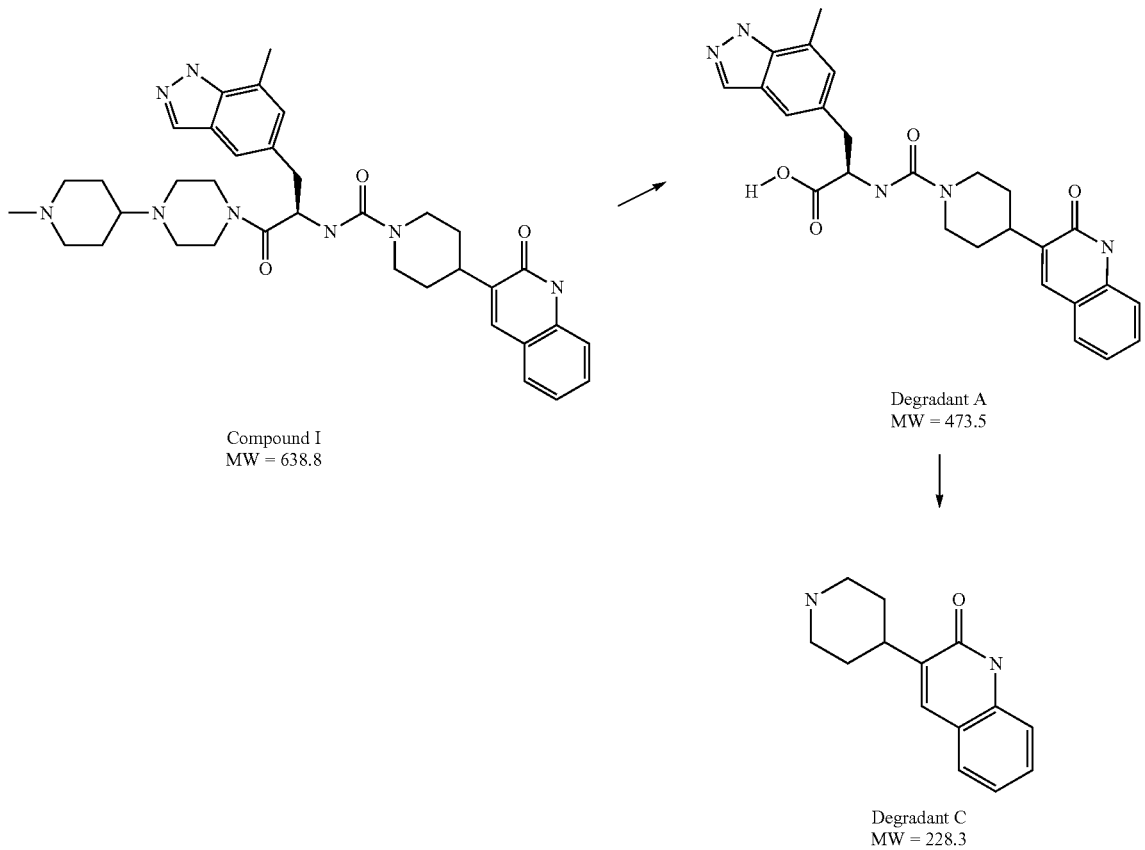

Scheme 6.

Compound I
MW = 638.8

Degradant A
MW = 473.5

Degradant C
MW = 228.3

Solution Stability: The effect of Temperature.

The effect of temperature is summarized in Table 5. The enhancement in degradation rate with temperature is largely due to the enhancement in hydrolysis. At the highest temperature degradation proceeded all the way to product C, but at the lower temperatures degradation stalled at product A (FIG. 2).

Solution Stability: The Effect of Light.

The effect of light on stability is summarized in Table 6. Seven degradants were noted for samples exposed to light, three of which did not appear in samples stored under any other condition. Hydrolysis (degradant A) was enhanced by exposure to light.

TABLE 6

Solution Stability and Light

| pH | Temperature (C.) | Light Condition | Total Degradants |
|----|------------------|-----------------|------------------|
| 5  | 25               | Dark            | 2.3%             |
| 5  | 25               | Light           | 72%              |

Solution Stability: The Effect of pH.

The effect of pH on the degradation rate is summarized in Table 7. The enhancement in degradation rate varied inversely with pH and was dominated by an enhancement in hydrolysis. At pH 4, degradation proceeded to hydrolysis product C, but at pH 5 and 6 degradation stalled at hydrolysis product A.

TABLE 7

Solution Stability and pH

| pH | Total Degradants |
|----|------------------|
| 4  | 12.5%            |
| 5  | 2.2%             |
| 6  | 0.62%            |

Solution Stability: The Effect of Buffer Concentration.

Higher concentrations of succinate buffer tended to produce a higher rate of hydrolysis to degradant A (Table 8).

TABLE 8

Solution Stability and Succinate Buffer Concentration

| pH | Total Degradants [Buffer] = 0.01M | Total Degradants [Buffer] = 0.05M |
|----|-----------------------------------|-----------------------------------|
| 5  | 1.8%                              | 2.2%                              |

Solution Stability: The Effect of Drug Concentration.

High drug load slowed the hydrolysis rate and limited hydrolysis to formation of degradant A (Table 9). Degradant G, which was only detected in the high concentration samples, did not markedly grow in concentration during the study and may simply be an impurity. Degradant J could only be detected at the final time point.

TABLE 9

Solution Stability and Compound I Concentration

| pH | Total Degradants [Drug] = 0.1 mg/ml | Total Degradants [Drug] = 40 mg/ml |
|----|-------------------------------------|------------------------------------|
| 4  | 12.5%                               | 8.6%                               |
| 5  | 2.2%                                | 1.5%                               |
| 6  | .62%                                | 0.5%                               |

Competition for [$^{125}$I]CGRP Binding

Binding Assay.

SK-N-MC cell membrane homogenate serves as the receptor source. Human neuroblastoma SK-N-MC cells are used for in vitro assays because they endogenously express the CGRP receptor with an identical sequence to the cloned human CGRP receptor (Aiyar et al., 2001). Cells are grown at 37° C. in 5% $CO_2$ in medium consisting of MEM with Earle's salts and L-glutamine supplemented with 10% fetal bovine serum to reach confluence. The cells are harvested by rinsing twice with phosphate-buffered saline and are incubated for 5-10 minutes at 4° C. in hypotonic lysis buffer consisting of 10 mM Tris (pH 7.4) and 5 mM EDTA. The cells are collected and transferred to polypropylene tubes and homogenized using a polytron. Homogenates are centrifuged at 32,000×g for 30 min. The pellets are resuspended in cold hypotonic lysis buffer with 0.1% mammalian protease inhibitor cocktail and assayed for protein concentration. The membrane homogenate is then aliquoted and stored at −80° C. until the day of assay.

The ability of Compound I to compete for the radiolabeled ([$^{125}$I]CGRP, Amersham Biosciences) endogenous peptide human alpha CGRP (hαCGRP) is measured using a radioligand competition assay. Compound I is first solubilized in and carried through serial dilutions using 100% DMSO. Compound is further diluted 25 fold into assay buffer (50 mM Tris-Cl pH 7.5, 5 mM $MgCl_2$, 0.005% Triton X-100) and transferred (50 µl) into 96 well assay plates. [$^{125}$I]-CGRP is diluted to 600 pM in assay buffer and a volume of 50 µl is added to each well (final concentration 15 pM in assay). SK-N-MC membrane pellets are thawed, diluted in assay buffer with fresh 0.1% mammalian protease inhibitor cocktail, and homogenized as previously described. Five to ten µg protein per well is then added in a volume of 100 µl. The assay plates are then incubated at room temperature (25° C.) for two hours. Assays are terminated by the addition of excess cold wash buffer (20 mM Tris-Cl pH 7.5, 0.1% BSA) immediately followed by filtration over glass fiber filters pre-soaked in 0.5% PEI. Non-specific binding is defined with 1 µM β-CGRP. Protein bound radioactivity is measured using a gamma scintillation counter. The $IC_{50}$ is defined as the concentration of compound required to inhibit 50% of radioligand binding.

Results.

Compound I displays concentration-dependent inhibition of [$^{125}$I]CGRP binding to the CGRP receptor endogenously expressed in SK-N-MC cell membranes. The mean K, is 22.7±1.6 pM.

Interaction with CGRP Peptide

Methods.

The nature of the interaction between the endogenous CGRP peptide and Compound I is studied in detail using saturation binding experiments. Briefly, the binding of [$^{125}$I] CGRP to the SK-N-MC cell membrane preparation is measured with increasing concentration of [$^{125}$I]CGRP without (control condition) or in the presence of (test conditions) one of the two concentrations (30 pM and 100 pM) of Compound I. Saturation data are analyzed with hyperbolic equations using Kell software (Biosoft, Cambridge, UK) to estimate dissociation constant ($K_d$) and the maximum number of binding sites ($B_{max}$). The impact of the addition of Compound I to the binding parameters ($K_d$, $B_{max}$) of [$^{125}$I]CGRP is measured and compared.

Results.

Compound I concentration-dependently increases the dissociation constant $K_d$ of [$^{125}$I]CGRP binding (decreases its affinity), without significantly changing the maximum number of binding sites of [$^{125}$I]CGRP binding ($B_{max}$). This indicates a competitive mechanism of inhibition by Compound I to the binding of [$^{125}$I]CGRP at the human receptor (Table 10).

TABLE 10

$K_d$, $B_{max}$ of [$^{125}$I]CGRP to the SK-N-MC Cell Membrane Preparation With or Without the Presence of Compound I.

|  | Control | 30 pM Compound I | 100 pM Compound I |
|---|---|---|---|
| Kd (pM) | 23.1 ± 5.0 | 58.0 ± 19.6 | 129.7 ± 31.9 |
| Bmax (fmol/mg protein) | 142.6 ± 10.6 | 112.1 ± 20.6 | 146.8 ± 6.4 |

Cellular Functional Assay—Cyclic AMP Assay

Methods.

The CGRP receptor complex is coupled to the Gs class of G proteins. Binding of CGRP to this complex leads to the production of cyclic AMP (adenosine 3'S'-cyclic monophosphate) via Gs-dependent activation of adenylate cyclase.

Functional antagonism by Compound I is determined by measuring its ability to inhibit CGRP-stimulated formation of cyclic AMP in attached whole SK-N-MC cells. SK-N-MC cells are incubated at room temperature with 0.3 nM CGRP alone for 30 minutes, or pre-incubated with various concentrations of Compound I for 15 minutes before the addition of 0.3 nM CGRP and then further incubated for 30 minutes. The Cyclic AMP (cAMP) produced is extracted using the "Lysis Reagent" and its concentration is determined by radioimmunoassay using RPA559 cAMP SPA Direct Screening Assay Kit (Amersham Pharmacia Biotech). $IC_{50}$ values are defined as the concentration of compound required to inhibit 50% of 0.3 nM CGRP-stimulated cAMP production. Ymax is defined as maximal percent inhibition of 0.3 nM CGRP-stimulated cAMP production.

Results.

Compound I displays concentration-dependent inhibition of CGRP-stimulated cAMP production in attached whole SK-N-MC cells, with an $IC_{50}$ of 38.6±4.2 pM, and a Ymax of 95.4 (±1.3) %. The maximal (ca. 100%) inhibition observed indicates full antagonism at the CGRP receptor.

Schild Analysis

Methods.

Schild analysis is used to characterize the nature of the antagonism of Compound I. The dose response of CGRP-stimulated cAMP production is generated either with CGRP alone, or with CGRP in the presence of various concentrations of Compound I. Specifically, dose-dependent cAMP stimulation by CGRP is assayed with or without five different concentrations of Compound I. The concentration of Compound I is plotted on the X-axis against the dose ratio minus 1 on the Y-axis (dose ratio is defined as the $EC_{50}$ of CGRP in the presence of Compound I divided by the $EC_{50}$ of CGRP alone). Linear regression is then performed with both X and Y axes log-transformed. A slope that does not differ significantly from unity (1) indicates competitive antagonism. $K_b$ is the antagonist dissociation constant.

Results.

Schild analysis for Compound I reveals a mean slope of 1.02±0.04 and mean antagonist dissociation constant $K_b$ of 21.5±9.4 pM. The parallel rightward shift of the CGRP concentration-response in the presence of increasing concentration of Compound I indicates competitive antagonism by Compound I of CGRP-stimulated cAMP production. The slope of 1.02 from the Schild plot further supports the competitive interaction between Compound I and CGRP function. $K_b$ of 21.5 pM is in agreement with the binding $K_i$ (22.7 pM).

Reversal of CGRP-Induced Dilation in Ex Vivo Human Intracranial Artery

To provide an ex vivo measure that mimics the clinical condition (where migraine-related CGRP release precedes initiation of therapy), vessels are first dilated by CGRP and then the dilation is reversed with Compound I. In this reversal protocol, antagonist post-treatment reverses CGRP-induced artery dilation (using a single agonist dose and multiple antagonist doses). In brief, wire mounted artery rings are contracted with potassium ion (to mimic endogenous tone), fully dilated with CGRP, and the dilation reversed with increasing concentrations of the CGRP antagonist Compound I. Compound I post-treatment is effective at reversing established CGRP-induced dilation of ex vivo human intracranial arteries.

Tissue Samples.

Autopsy samples of human arteries are obtained from tissue procurement vendors. All vessels are transported in ice-cold HEPES buffer (composition in mM: NaCl 130, KCl 4, $KH_2PO_4$ 1.2, $MgSO_4$ 1.2, $CaCl_2$ 1.8, Glucose 6, $NaHCO_3$ 4, HEPES 10, EDTA 0.025). Upon receipt, the vessels are placed in cold Kreb's buffer (composition in mM: NaCl 118.4, KCl 4.7, $KH_2PO4$ 1.2, $MgSO_4$ 1.2, $CaCl_2$ 1.8, Glucose 10.1, $NaHCO_3$ 25) saturated with carbogen (5% $CO_2$ and 95% oxygen).

Methods.

The vessels are cleaned of connective tissues and cut into cylindrical segments of 4-5 mm in length. The vessels are then mounted in tissue baths between two stainless steel hooks; one of which is fixed and the other of which is connected to a force displacement transducer. The vessel tension is continuously recorded using a data acquisition system (Powerlab, AD Instruments, Mountain View, Calif.). The tissue baths containing Krebs buffer and mounted vessels are controlled for temperature (37° C.) and pH (7.4) and continuously bubbled with carbogen. The artery segments are allowed to equilibrate for about 30-45 minutes until a stable resting tone (0.25 to 0.5 g) is achieved. Prior to the assay, vessels are primed (conditioned) with 100 mM KCl and subsequently washed.

To test the anti-dilatory effect of Compound I, vessels are first contracted with 10 mM potassium chloride (KCl) to mimic endogenous tone, then fully dilated with 1 nM hαCGRP, and finally the dilation is reversed by the cumulative addition of increasing concentrations of Compound I in half log units (allowing calculation of $EC_{50}$'s). At each concentration, the effects of the drugs are expressed as % reversal of CGRP-induced dilation in each vessel. Data analysis is performed for each vessel individually, fitting the concentration-response data to a four parameter logistic function by non-linear regression analysis, to estimate the $EC_{50}$ values.

Results.

Compound I shows potent and full reversal of CGRP-induced dilation of ex vivo human intracranial arteries with $EC_{50}$=880±50 μM.

Schild Analysis: Inhibition of CGRP Concentration-Response Curve in Ex Vivo Human Intracranial Artery To assess functional antagonism against a range of CGRP concentrations, Compound I is pre-incubated with individual artery rings in the tissue bath and then a CGRP concentration-response curve is generated to achieve complete dilation (using multiple agonist and multiple antagonist doses). Higher concentrations of antagonist produce a 'right-shift' in the CGRP concentration-response curve, requiring greater concentrations of agonist to overcome the presence of antagonist and achieve full dilation. In short, wire mounted artery rings are pre-incubated with antagonist, then contracted with KCl (to mimic endogenous tone), and followed by addition of increasing concentrations of CGRP to achieve full relaxation. Compound I pretreatment is effective at inhibiting CGRP-induced dilation of ex vivo human intracranial arteries, and displays a parallel rightward shift of the CGRP concentration-response curve.

Methods.

Each wire mounted artery ring is pre-incubated for 30 min with a single concentration (0.1-30 nM) of the antagonist Compound I, then contracted with 10 mM KCl (to mimic endogenous tone), followed by addition of increasing concentrations of CGRP to achieve full relaxation. The KCl contraction is allowed to stabilize, such that total antagonist pretreatment time is approximately 45 min prior to application of CGRP.

Results.

Compound I produces a parallel rightward shift of the CGRP concentration-response curve in ex vivo human intracranial arteries. Schild analysis reveals a $K_b$ of 91 pM. These results compare favorably to the in vitro binding ($K_i$=22.7 pM) and functional ($K_b$=21.5 pM) assays.

In Vivo Efficacy of Compound I in Marmoset Facial Blood Flow

To evaluate the in vivo efficacy of novel CGRP receptor antagonists, marmosets receive a series of four intravenous injections of hαCGRP (at 45 min intervals). The first serves as a baseline control, and is followed by subcutaneous delivery of test article. The subsequent three CGRP challenges provide an assessment of functional CGRP antagonism in vivo. In the present study, Compound I demonstrated robust, lasting CGRP antagonism.

Methods.

Marmosets are anesthetized and facial blood flow is increased by intravenous (IV) administration of hαCGRP at 45 min intervals (−30, 15, 60 & 105 min) The effect of test compound, delivered at 0 min, on the hαCGRP-induced changes in facial blood flow is measured by laser Doppler flowmetry. Effective compounds would suppress the hαCGRP-induced increase in facial blood flow seen at 15, 60 & 105 min (as compared to the baseline hαCGRP effect seen at −30 min).

Subjects:

Adult male and female common marmosets (Callithrix jacchus) weighing 350-650 g serve as subjects.

Anesthesia and Preparation:

Animals are anesthetized by isoflurane inhalation in an induction chamber (4-5% rapid induction, maintained with 1-2.5%; Solomon et al., 1999). Anesthesia is maintained by delivering a constant supply of air:oxygen (50:50) and isoflurane via intubation and ventilation (with blood gas monitoring). Body temperature is maintained at 38±0.5° C. by placement on an automated temperature controlled surface with rectal probe. A small area of fur (approx. 1.5 cm square) is removed from one or both sides of the face by application of a depilatory cream and/or shaving. Surgical areas are clipped and prepared with betadine. An IV line is placed in the saphenous vein for the administration of test compounds and the CGRP receptor agonist hαCGRP. Additionally this IV line provides for withdrawal of blood samples (max 2.5 ml, 10%) for blood gas monitoring and analysis of compound plasma levels. A solution of 5% dextrose is administered IV in order to maintain blood sugar levels. Anesthesia depth is monitored by measuring blood pressure and heart rate using a non-invasive arm cuff method and a pulse oximeter, respectively. Guanethidine 5-10 mg/kg IV, supplemented with 5 mg/kg IV as needed, is given to stabilize the peak flux in facial blood flow which otherwise shows progressive reduction following repeated stimulation (Escott et al., 1995). Microvascular blood flow is monitored by attaching a self adhesive laser Doppler flow probe to the facial skin. The probe records the number of red blood cells crossing the path of two laser beams, multiplied by their velocity (reported as changes in flux).

Drug Delivery:

Test compounds are administered SC (0.1-0.6 ml/kg) in the nape of the neck. The CGRP-receptor agonist, hαCGRP is delivered IV (1 ml/kg) at a dose of 10 µg/kg.

Testing Protocol:

To assess in vivo efficacy and duration of action, a control increase in facial blood flow is induced by administration of hαCGRP (10 µg/kg IV) 30 min prior (−0.5 hr) to drug delivery. Compound I is then administered at time zero (0 min) and repeat hαCGRP are delivered at 45 min intervals for ~2 hr (data collected at 0.25, 1 and 1.75 hrs post-dose). Compound I is dosed at 0.003, 0.01 and 0.03 mg/kg, SC. Plasma samples are obtained just before each hαCGRP administration. Following testing, animals are returned to the transport cage which is placed on a temperature controlled surface that keep the animals warm until fully awake and ambulatory. Animals may be tested again after a 14-21 day rest and washout period.

Results.

Compound I (0.003-0.03 mg/kg, SC) shows dose-dependent inhibition of CGRP-induced increases in marmoset facial blood flow. Robust (53-80%) inhibition is observed at 0.03 mg/kg at 0.25, 1 and 1.75 hr post-dose. Significant (35-40%) inhibition is seen across all post-dose test times at 0.01 mg/kg. At 0.003 mg/kg, a mild (20%) but significant inhibition is observed at 0.25 hr, with no effect at later test times.

Comparing efficacy vs. exposure, plasma levels ≧8 nM are associated with significant in vivo efficacy and levels ≧25 nM with maximal efficacy for Compound I.

Intranasal Irritation Studies in Rats

Compound I and Compound III: One-Week Comparative Intranasal Irritation Study in Rats.

This study was conducted to compare potential nasal irritation of Compound I to Compound III when given intranasally to male rats for 1 week. Male rats (10/group) were instilled intranasally with Compound I or Compound III solutions (25, 75 or 175 mg/L in 225 mM succinic acid, 0.02% benzalkonium chloride, 1.25% anhydrous dextrose, pH 5.8-6.2) once daily at a dose volume of 100 µL/nostril. Using this dosing paradigm, fixed doses of 5, 15 or 35 mg of test article were delivered daily. As a consequence, dosages normalized to body weight decreased with time as the rats grew. One control group was given succinate vehicle and a sham control group was given saline by intranasal instillation. Parameters evaluated included clinical observations, body weight, food consumption, toxicokinetics, and histological evaluation of nasal tissues.

Values for toxicokinetic parameters are shown in Table 11.

TABLE 11

Toxicokinetic data derived for Compound I.

| | Compound I |||||| 
|---|---|---|---|---|---|---|
| | Dose, mg ||||||
| | 5 || 15 || 35 ||
| | Dose, mg/cm$^{2(3)}$ ||||||
| | 0.357 || 1.07 || 2.50 ||
| Parameter | Day 0 | Day 6 | Day 0 | Day 6 | Day 0 | Day 6 |
| Mean Dosage (mg/kg) | 21 | 19 | 62 | 56 | 144 | 132 |
| Mean Cmax (µM) | 0.33 | 0.66 | 2.2 | 0.83 | 1.5 | 1.2 |
| Composite AUC$_{0-24\,h}$ (µM · h) | 1.6 | 2.6 | 4.6 | 5.2 | 7.9 | 5.4 |
| Mean Tmax (h) | 0.50 | 1.0 | 1.0 | 0.50 | 2.0 | 1.0 |
| Mean T1/2 (h) | 7.1 | 5.6 | 5.1 | 6.7 | ND$^1$ | 6.0 |
| Mean C$_{24\,h}$ (µM) | 0.022 | 0.015 | 0.017 | 0.059 | 0.12 | 0.036 |

$^1$Not determined because of prolonged exposure.
$^2$Absolute bioavailability based on an AUC$_{0-24\,h}$ of 7.7 µM · h in rats following intravenous administration of 1 mg/kg.
$^{(3)}$Estimated rat nasal mucosal surface area = 14 cm$^2$ Intranasal dosing of Compound I provided systemic exposure in rats out to 24 hrs, and little difference was observed between the first and last days of dosing in this 1-week study.

Intranasal administration of Compound I was well tolerated; in-life findings were limited to increased salivation in all dose groups and vehicle controls, and was possibly related to the excessively large dosing volume used for the study. Salivation not observed in rats given saline.

Nasal irritation was observed for both compounds but Compound I clearly caused less olfactory epithelial atrophy than Compound III over the dose range (Table 12). The type of lesion observed was consistent with prior observations made for Compound II. The severity and incidence of nasal findings demonstrated that Compound I had a superior nasal toxicity profile to that of Compound III.

TABLE 12

Incidence and severity Olfactory Epithelial Atrophy following Nasal Instillation of Compound III or Compound I in Rats

| | Dose (mg) ||||||
|---|---|---|---|---|---|---|
| | 5 || 15 || 35 ||
| | Dose, (mg/cm$^2$)$^{(1)}$ ||||||
| | 0.357 || 1.07 || 2.50 ||
| Severity | Compound III | Compound I | Compound III | Compound I | Compound III | Compound I |
| None | 1 | 8 | 1 | 1 | 3 | 4 |
| Minimal | 6 | 1 | 0 | 6 | 0 | 3 |
| Mild | 2 | 0 | 2 | 2 | 2 | 2 |
| Moderate | 0 | 0 | 6 | 0 | 3 | 0 |
| Marked | 0 | 0 | 0 | 0 | 1 | 0 |

$^{(1)}$Estimated total nasal mucosal surface area of the rat is 14 cm$^2$

Compound I and Compound II: One-Week Exploratory Intranasal Irritation Study in Rats.

Compound I and Compound II were also compared directly for intranasal irritation. Male rats (6/group) were instilled intranasally with Compound I or Compound II solutions (75 or 175 mg/L) in 225 mM succinic acid, 1.25% anhydrous dextrose, pH 5.8-6.2) once daily at a dose volumes of 12.5, 25 or 100 µL/nostril. The only endpoint evaluated in this study was histological evaluation of the nasal turbinates.

The olfactory epithelial atrophy caused by Compound I was clearly less severe than that produced by Compound II at each dose (volume×concentration) evaluated (Table 13).

TABLE 13

Olfactory epithelial toxicity, severity scores for Compound I and Compound II.

| Compound | volume/nostril | 12.5 µL || 25 µL || 100 µL ||
|---|---|---|---|---|---|---|---|
| | mg/ml | 75 | 175 | 75 | 175 | 75 | 175 |
| | mg/rat/day | 1.875 | 4.375 | 3.75 | 8.75 | 15 | 35 |
| | mg/cm$^{2(1)}$ | 0.134 | 0.313 | 0.268 | 0.625 | 1.071 | 2.500 |
| Compound I | None | 5 | 5 | 2 | 4 | | |
| | Minimal | | | 3 | 1 | | |
| | Slight | | | | | 5 | 1 |
| | Mild | | | | | | 4 |
| Compound II | None | 3 | 3 | 2 | 1 | | |
| | Minimal | | 1 | 2 | 3 | | |
| | Slight | 1 | | 1 | 1 | 4 | |
| | Mild | 1 | 1 | | | 1 | 2 |
| | Moderate | | | | | | 3 |

Severity of lesions was assessed on a 1 through 5 scale. Values correspond to the number of animals showing each severity grade. Scores include olfactory epithelial atrophy, exudate, and single-cell necrosis. Each type of injury was scored separately and the most severe score is shown here. There were no lesions in the vehicle-dosed animals. n = 5 animals per group. No exposure data was obtained in this comparative irritation study.

$^{(1)}$Estimated total nasal mucosal surface area of the rat is 14 cm$^2$

The dose-response relationship of Compound II was consistent with that observed in other studies. Both increased volume and increased concentration contributed to more significant nasal toxicity but concentration is likely the more important factor.

In summary, Compound I demonstrated superiority to Compound II, with respect to nasal irritation.

Potential for Nasal Delivery.

The intra-nasal (IN) route of administration for CGRP antagonists is attractive as it affords non-invasive delivery with the potential for rapid onset of action. The highly permeable nasal epithelial barrier, well perfused mucosal tissue, and limited metabolic capacity/tissue residence time are potentially useful features that support intranasal delivery of a compound like Compound I that exhibits very poor oral absorption.

The feasibility of nasal delivery was assessed in the IN rabbit model by comparing the plasma concentration-time profiles and pharmacokinetic parameters (Cmax, Tmax, AUC and bioavailability) for nasally delivered Compound I to that delivered by the IV route. The dosing solution concentration and delivery volume are included in the data tables for each study. Vehicle compositions are described in the footnotes below the table.

Methods.

Groups of three male New Zealand White rabbits, ranging in weight from 3-3.5 kg, received a single dose of drug in one of the following treatments: 0.5 mg/kg IV bolus injection over 30 seconds, or 0.3-3 mg/kg IN administered with a syringe microsprayer. Prior to IN dosing, rabbits were lightly sedated to effect with the inhalant anesthetic, Sevoflurane. The rabbits regained consciousness in 2-5 min. Serial blood samples were collected in heparin-containing vacutainers at predose, 2, 5, 10, 15, 30 min and 1, 2, 4, 6, and 24 hours post-dose. Blood samples were immediately centrifuged at 4° C. and the separated plasma stored at −80° C. until further analysis by the LC/MS/MS assay.

Results.

The pharmacokinetic profile indicates that Compound I is rapidly absorbed from the nasal cavity of rabbits when sprayed as a solution. The time to reach peak concentrations ($T_{max}$) occurs within 0.2-0.3 h (15-20 min) at all doses studied. The absolute bioavailability at 0.3, 1, and 3 mg/kg ranged from 13 to 30% and the Cmax ranged from 0.12 to 2.0 µM (Table 14).

TABLE 14

Pharmacokinetic Parameters for Compound I in the Rabbit after IV and IN Administration.

| Parameter | IV (n = 3, Mean ± SD) | IN (low dose) (n = 3, Mean ± SD) | IN (mid-dose) (n = 3, Mean ± SD) | IN (high dose) (n = 3, Mean ± SD) |
|---|---|---|---|---|
| Dose (mg/kg) | 0.5 | 0.3 | 1.0 | 3.0 |
| Dosing volume (µl) | | 100 (50/nostril) | 100 (50/nostril) | 100 (50/nostril) |
| Dosing concentration (mg/ml) | 5 | 10 | 30 | 100 |
| Cmax (µM) | 13.7 ± 1.8 | 0.12 ± 0.69 | 0.55 ± 0.26 | 2.03 ± 1.0 |
| Tmax (h) | | 0.25 | 0.25 | 0.33 |
| $AUC_{tot}$ (µM · h) | 1.8 ± 0.58 | 0.14 ± 0.07 | 0.69 ± 0.33 | 3.27 ± 1.17 |
| Cl (ml/min/kg) | 7.9 ± 3.0 | — | — | — |
| Vss (L/kg) | 0.16 ± 0.01 | — | — | — |
| $T_{1/2}$ (h) | 1.3 ± 0.26 | — | — | — |
| MRT (h) | 0.38 ± 0.15 | — | — | — |
| Bioavailability (F %) | — | 12.5 ± 6.56 | 18.8 ± 8.96 | 30.2 ± 10.82 |

IV formulation: 50 mM succinate buffer/D5W vehicle, pH 5.
IN formulation: 50 mM succinate buffer, pH 5-6.

IN absorption of Compound I in the rabbit was very rapid. Plasma levels >10 nM were measured within 5 min. The drug was detected in plasma for at least 6 h post-dose and up to 24 hr at the high dose.

Previously, with Compound II there was greater deviation from linearity when intranasal delivery volume rather than dosing concentration was changed. By keeping Compound I delivery volume constant and varying the dosing solution concentration, the IN AUC and Cmax showed a trend towards dose-dependent linearity (Table 15). The variability in these parameters also increased with dose. On closer examination, the IN bioavailability appeared to increase with dose (or dosing concentration) for the three doses tested (Table 15).

TABLE 15

Dose Linearity of IN Compound I in Rabbits

| Dose (mg/kg) (n = 3, mean ± SD) | Cmax (µM) | $AUC_{tot}$ (µM · h) |
|---|---|---|
| 0.3 | 0.12 ± 0.07 | 0.14 ± 0.07 |
| 1.0 | 0.55 ± 0.26 | 0.69 ± 0.33 |
| 3.0 | 2.03 ± 1.0 | 3.27 ± 1.17 |
| Trend line $R^2$ | 0.99 | 0.99 |

Dosing concentrations were 10, 30, and 100 mg/ml in 50 mM succinate buffer vehicle, pH 5.

In summary, the intra-nasal route of administration for Compound I provides rapid systemic absorption and relatively prolonged plasma levels compared to the oral route. The high aqueous solubility and improved solution stability favorably support the viability of a nasal spray product in an appropriate spray device. The delivery of drug solution and its deposition in the nasal cavity in humans is expected to be more robust and reproducible than that possible with preclinical IN animal models. Compound I formulations are projected to be delivered in reusable multi-dose or disposable unit dose nasal spray devices.

Pharmaceutical Compositions and Methods of Treatment

Another aspect of the invention is a pharmaceutical composition comprising Compound I with a pharmaceutically acceptable adjuvant, carrier, or diluent.

Compound I will generally be given as pharmaceutical composition comprised of a therapeutically effective amount of a Compound I, or a pharmaceutically acceptable salt, and a pharmaceutically acceptable carrier and may contain conventional exipients. A therapeutically effective amount is the amount needed to provide a meaningful patient benefit as determined by practitioners in that art. Pharmaceutically acceptable carriers are those conventionally known carriers having acceptable safety profiles. Compositions encompass all common solid and liquid forms including capsules, tablets, losenges, and powders as well as liquid suspensions, syrups, elixers, and solutions. Solid compositions may by formed in timed or sustained released formulations. Compositions are made using common formulation techniques and conventional excipients (such as binding and wetting agents) and vehicles (such as water and alcohols).

Solid compositions are normally formulated in dosage units providing from about 1 to about 1000 mg of the active ingredient per dose. Some examples of solid dosage units are 0.1 mg, 1 mg, 10 mg, 100 mg, 500 mg, and 1000 mg. Liquid compositions are generally in a unit dosage range of 1-100 mg/mL. Some examples of liquid dosage units are 0.1 mg/mL, 1 mg/mL, 10 mg/mL, 25 mg/mL, 50 mg/mL, and 100 mg/mL.

The invention encompasses all conventional modes of administration including oral, parenteral, intranasal, sublingual, and transdermal methods. Typically, the daily dose will be 0.01-100 mg/kg body weight daily. Generally, more compound is required orally and less parenterally. The specific dosing regime, however, should be determined by a physician using sound medical judgement.

Another aspect of the invention is intranasal administration.

Inhibitors at the receptor level to CGRP are postulated to be useful in pathophysiologic conditions where excessive CGRP receptor activation has occurred. Some of these include neurogenic vasodilation, neurogenic inflammation, migraine, cluster headache and other headaches, thermal injury, circulatory shock, menopausal flushing, and asthma. CGRP receptor activation has been implicated in the pathogenesis of migraine headache (Edvinsson L. CNS Drugs 2001, 15(10), 745-53; Williamson, D. J. Microsc. Res. Tech. 2001, 53, 167-178.; Grant, A. D. Brit. J. Pharmacol. 2002, 135, 356-362.). Serum levels of CGRP are elevated during migraine (Goadsby P. J. et al. Ann. Neurol. 1990, 28, 183-7) and treatment with anti-migraine drugs returns CGRP levels to normal coincident with alleviation of headache (Gallai V. et al. Cephalalgia 1995, 15, 384-90). Migraineurs exhibit elevated basal CGRP levels compared to controls (Ashina M. et al., Pain 2000, 86(1-2), 133-8). Intravenous CGRP infusion produces lasting headache in migraineurs (Lassen L. H. et al. Cephalalgia. 2002, 22(1), 54-61). Preclinical studies in dog and rat report that systemic CGRP blockade with the peptide antagonist CGRP (8-37) does not alter resting systemic hemodynamics nor regional blood flow (Shen, Y-T. et al. J. Pharmacol. Exp. Ther. 2001, 298, 551-8). Thus, CGRP-receptor antagonists may present a novel treatment for migraine that avoids the cardiovascular liabilities of active vasoconstriction associated with non-selective 5-HT1B/1D agonists, "triptans" (e.g., sumatriptan).

Another aspect of the invention is a method of inhibiting the CGRP receptor comprising contacting the CGRP receptor with a compound of formula I or a pharmaceutically acceptable salt thereof.

Another aspect of the invention is a method for treating conditions associated with aberrant levels of CGRP or CGRP receptor signaling comprising the administration of a therapeutically effective amount of a compound of formula I to a patient.

Another aspect of the invention is the use of a compound of formula I in the manufacture of a medicament for the treatment of conditions related to aberrant levels of CGRP or CGRP receptor signaling.

Another aspect of the invention is a method of treating migraine or headache.

Another aspect of the invention is a method of treating neuropathic pain.

Another aspect of the invention relates to a method of treating inflammation (particularly neurogenic inflammation), pain, thermal injury, circulatory shock, diabetes, Reynaud's syndrome, peripheral arterial insufficiency, subarachnoid/cranial hemorrhage, tumor growth, flushing associated with menopause and other conditions the treatment of which can be effected by the antagonism of the CGRP receptor by the administration of pharmaceutical compositions comprising a compound of formula I as defined herein.

Another aspect of the invention relates to methods selected from the group consisting of (a) immune regulation in gut mucosa (b) protective effect against cardiac anaphylactic injury (c) stimulating or preventing interleukin-1b(IL-1b)-stimulation of bone resorption (d) modulating expression of NK1 receptors in spinal neurons and (e) airway inflammatory diseases and chronic obstructive pulmonary disease including asthma. See (a) Calcitonin Receptor-Like Receptor Is Expressed on Gastrointestinal Immune Cells. Hagner, Stefanie; Knauer, Jens; Haberberger, Rainer; Goeke, Burkhard; Voigt, Karlheinz; McGregor, Gerard Patrick. Institute of Physiology, Philipps University, Marburg, Germany. Digestion (2002), 66(4), 197-203; (b) Protective effects of calcitonin gene-related peptide-mediated evodiamine on guinea-pig cardiac anaphylaxis. Rang, Wei-Qing; Du, Yan-Hua; Hu, Chang-Ping; Ye, Feng; Tan, Gui-Shan; Deng, Han-Wu; Li, Yuan-Jian. School of Pharmaceutical Sciences, Department of Pharmacology, Central South University, Xiang-Ya Road 88, Changsha, Hunan, Naunyn-Schmiedeberg's Archives of Pharmacology (2003), 367(3), 306-311; (c) The experimental study on the effect calcitonin gene-related peptide on bone resorption mediated by interleukin-1. Lian, Kai; Du, Jingyuan; Rao, Zhenyu; Luo, Huaican. Department of Orthopedics, Xiehe Hospital, Tongji Medical College, Huazhong University of Science and Technology, Wuhan, Peop. Rep. China. Journal of Tongji Medical University (2001), 21(4), 304-307, (d) Calcitonin gene-related Peptide regulates expression of neurokinin) receptors by rat spinal neurons. Seybold V S, McCarson K E, Mermelstein P G, Groth R D, Abrahams L G. J. Neurosci. 2003 23 (5): 1816-1824. Department of Neuroscience, University of Minnesota, Minneapolis, Minn. 55455, and Department of Pharmacology, Toxicology, and Therapeutics, University of Kansas Medical Center, Kansas City, Kans. 66160 (e) Attenuation of antigen-induced airway hyperresponsiveness in CGRP-deficient mice. Aoki-Nagase, Tomoko; Nagase, Takahide; Oh-Hashi, Yoshio; Shindo, Takayuki; Kurihara, Yukiko; Yamaguchi, Yasuhiro; Yamamoto, Hiroshi; Tomita, Tetsuji; Ohga, Eijiro; Nagai, Ryozo; Kurihara, Hiroki; Ouchi, Yasuyoshi. Department of Geriatric Medicine, Graduate School of Medicine, University of Tokyo, Tokyo, Japan. American Journal of Physiology (2002), 283(5,Pt. 1), L963-L970; (f) Calcitonin gene-related peptide as inflammatory mediator. Springer, Jochen; Geppetti, Pierangelo; Fischer, Axel; Groneberg, David A. Charite Campus-Virchow, Department of Pediatric Pneumology and Immunology, Division of Allergy Research, Humboldt-University Berlin, Berlin, Germany. Pulmonary Pharmacology & Therapeutics (2003), 16(3), 121-130; and (g) Pharmacological targets for the inhibition of neurogenic inflammation. Helyes, Zsuzsanna; Pinter, Erika; Nemeth, Jozsef; Szolcsanyi, Janos. Department of Pharmacology and Pharmacotherapy, Faculty of Medicine, University of Pecs, Pecs, Hung. Current Medicinal Chemistry: Anti-Inflammatory & Anti-Allergy Agents (2003), 2(2), 191-218.

Another aspect of this invention relates to a method of treatment for cancer and proliferative diseases and conditions. CGRP antagonists have also been proposed to show utility in the treatment of malignant disease, particularly against gliomas and breast cancer that metastasizes to the brain. CGRP antagonists may be especially useful against hypoxic tumors and in the prevention of metastatic implantation. See PCT application publication WO2010006168.

Another aspect of this invention relates to a method of treatment using combinations of Formula I compounds with one or more agents selected from the group consisting of COX-2 inhibitors, NSAIDS, aspirin, acetaminophen, triptans, ergotamine and caffeine for the treatment of migraine.

"Migraine," "headache," and related terms are as understood by medical practitioners. Migraine encompasses all classes of migraine including common, classic, cluster, fulgurating, hemiplegic, opthalmoplegic, and opthomalmic.

"Therapeutically effective" means there is a meaningful patient benefit as understood by medical practitioners.

"Patient" means a person who may benefit from treatment as determined by medical practitioners.

It will be evident to one skilled in the art that the present disclosure is not limited to the foregoing illustrative example, and that it can be embodied in other specific forms without departing from the essential attributes thereof. It is therefore desired that the examples be considered in all respects as illustrative and not restrictive, reference being made to the appended claims, rather than to the foregoing examples, and all changes which come within the meaning and range of equivalency of the claims are therefore intended to be embraced therein.

We claim:

1. The compound (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide, which has the following structure:

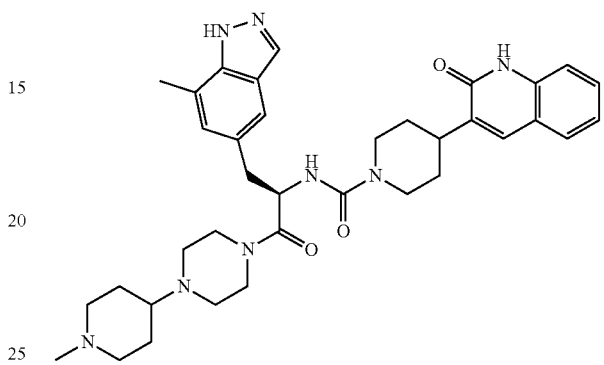

or a pharmaceutically acceptable salt thereof.

2. A pharmaceutical composition comprising a therapeutically effective amount of (R)—N-(3-(7-methyl-1H-indazol-5-yl)-1-(4-(1-methylpiperidin-4-yl)piperazin-1-yl)-1-oxopropan-2-yl)-4-(2-oxo-1,2-dihydroquinolin-3-yl)piperidine-1-carboxamide in association with a pharmaceutically acceptable adjuvant, carrier, or diluent.

3. A method of treating migraine comprising the administration of a therapeutically effective amount of a compound of claim 1, or a pharmaceutically acceptable salt thereof, to a patient.

\* \* \* \* \*